(12) United States Patent
Ryu et al.

(10) Patent No.: US 11,844,844 B2
(45) Date of Patent: Dec. 19, 2023

(54) FUSION PROTEIN COMPRISING GLUTATHIONE-S-TRANSFERASE AND PROTEIN HAVING BINDING AFFINITY TARGET CELL OR TARGET PROTEIN, AND USE THEREOF

(71) Applicant: UNIST(ULSAN NATIONAL INSTITUTE OF SCIENCE AND TECHNOLOGY), Ulsan (KR)

(72) Inventors: Ja Hyoung Ryu, Ulsan (KR); Joon Yong Oh, Ulsan (KR); Han Sol Kim, Ulsan (KR); Chae Kyu Kim, Ulsan (KR); Se Byung Kang, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 525 days.

(21) Appl. No.: 16/767,804

(22) PCT Filed: Nov. 28, 2018

(86) PCT No.: PCT/KR2018/014782
§ 371 (c)(1),
(2) Date: May 28, 2020

(87) PCT Pub. No.: WO2019/107896
PCT Pub. Date: Jun. 6, 2019

(65) Prior Publication Data
US 2021/0000971 A1    Jan. 7, 2021

(30) Foreign Application Priority Data
Nov. 28, 2017  (KR) .................. 10-2017-0159936

(51) Int. Cl.
A61K 47/68   (2017.01)
A61K 47/69   (2017.01)
(Continued)

(52) U.S. Cl.
CPC ...... *A61K 47/6889* (2017.08); *A61K 31/4745* (2013.01); *A61K 47/64* (2017.08);
(Continued)

(58) Field of Classification Search
None
See application file for complete search history.

(56) References Cited

U.S. PATENT DOCUMENTS
5,654,176 A    8/1997   Smith

FOREIGN PATENT DOCUMENTS
| KR | 10-2017-0028637 |   | 3/2017 |
| KR | 1020170028637   | * | 3/2017 |
| WO | WO 93/19091     |   | 9/1993 |

OTHER PUBLICATIONS

Oh et al., Nat Commun 9, 4548 (2018) https://doi.org/10.1038/s41467-018-06979-4 (Year: 2018).*

(Continued)

*Primary Examiner* — Karl J Puttlitz
(74) *Attorney, Agent, or Firm* — Klarquist Sparkman, LLP

(57) ABSTRACT

Provided are a fusion protein including glutathione-S-transferase and a protein having binding affinity for a target cell or a target protein, and use thereof as a drug delivery carrier and a pharmaceutical composition. The fusion protein and the drug delivery carrier including the same according to an aspect may sustain an in vivo residence time, and may also have improved target cell-targeting ability, and thus may be effectively delivered to target cells. Accordingly, it may be usefully applied to a targeted therapeutic agent.

12 Claims, 39 Drawing Sheets
Specification includes a Sequence Listing.

(51) Int. Cl.

| | |
|---|---|
| *A61K 47/64* | (2017.01) |
| *A61P 35/00* | (2006.01) |
| *A61K 31/4745* | (2006.01) |
| *C07K 16/28* | (2006.01) |
| *C07K 16/32* | (2006.01) |
| *C12N 9/10* | (2006.01) |

(52) U.S. Cl.
 CPC ...... *A61K 47/6849* (2017.08); *A61K 47/6929* (2017.08); *A61P 35/00* (2018.01); *C07K 16/2863* (2013.01); *C07K 16/32* (2013.01); *C12N 9/1088* (2013.01); *C07K 2318/00* (2013.01); *C07K 2319/70* (2013.01); *C07K 2319/74* (2013.01)

(56) References Cited

OTHER PUBLICATIONS

Ma et al. Protein Conjugation to Nanoparticles by Designer Affinity Tags. Materials Today: Proceedings. 2017 (electronic publication on Sep. 1, 2017), vol. 4, pp. 6923-6929 (Year: 2017).*
Machine translation of KR20170028637A, downloaded Aug. 3, 2022 from https://patents.google.com/patent/KR20170028637A/en?oq=20170028637 (Year: 2017).*
Ha et al., Anal. Chem. 2007, 79, 2, 546-556 (Year: 2007).*
Lofblom et al., FEBS Letters 584:2670-2680, 2010 (Year: 2010).*
Stahl et al., Trends Biotechnol 35(8):691-712, e-published May 14, 2017 (Year: 2017).*
Cook et al., "Insertion of inter-domain linkers improves expression and bioactivity of Zygote arrest (Zar) fusion proteins," *Protein Eng Des Sel* 30(4): 313-319, 2017.
Hu et al., "A flexible peptide linker enhances the immunoreactivity of two copies HBsAg preSI (21-47) fusion protein," *J Biotechnol* 107(1): pp. 83-90, 2004.
Nishi et al., "Collagen-binding growth factors: Production and characterization of functional fusion proteins having a collagen-binding domain," *Proc Natl Acad Sci USA* 95: 7018-7023, 1998.
Oh et al., "Cloaking nanoparticles with protein corona shield for targeted drug delivery" *Nat Commun* (9)1: 4578, 2018.
Supplementary European Search Report for related European Application No. 18884380.9, dated Nov. 16, 2020 (9 pages).
Ha et al., "Oriented Immobilization of Antibodies with GST-Fused Multiple Fc-Specific B-Domains on a Gold Surface," *Anal. Chem.*, vol. 79:546-556, 2007.
Ma et al., "Protein Conjugation to Nanoparticles by Designer Affinity Tags," *Materials Today: Proceedings*, vol. 4:6923-6929, 2017.
Mahmoudi et al., "Emerging Understanding of the Protein Corona at the Nano-Bio Interfaces," *Nano Today*, vol. 11:817-832, 2016.
Moon et al., "Plug-and-Playable Fluorescent Cell Imaging Modular Toolkits Using the Bacterial Superglue, SpyTag/SpyCatcher," *Chem. Commun.*, vol. 52:14051-14054, 2016.
Office Action for Korea Application No. 2017-0159936, dated Nov. 26, 2018 (in Korean with English machine translation).
Pan et al., "Glutathione (GSH)-Decorated Magnetic Nanoparticles for Binding Glutathione-S-Transferase (GST) Fusion Protein and Manipulating Live Cells," *Chem. Sci.*, vol. 2:945-948, 2011.
Vinluan et al., "Glutathione-Coated Luminescent Gold Nanoparticles: A Surface Ligand for Minimizing Serum Protein Adsorption," *ACS Appl. Mater. Interfaces*, vol. 6:11829-11833, 2014.

\* cited by examiner

GST-HER2

GST-EGFR

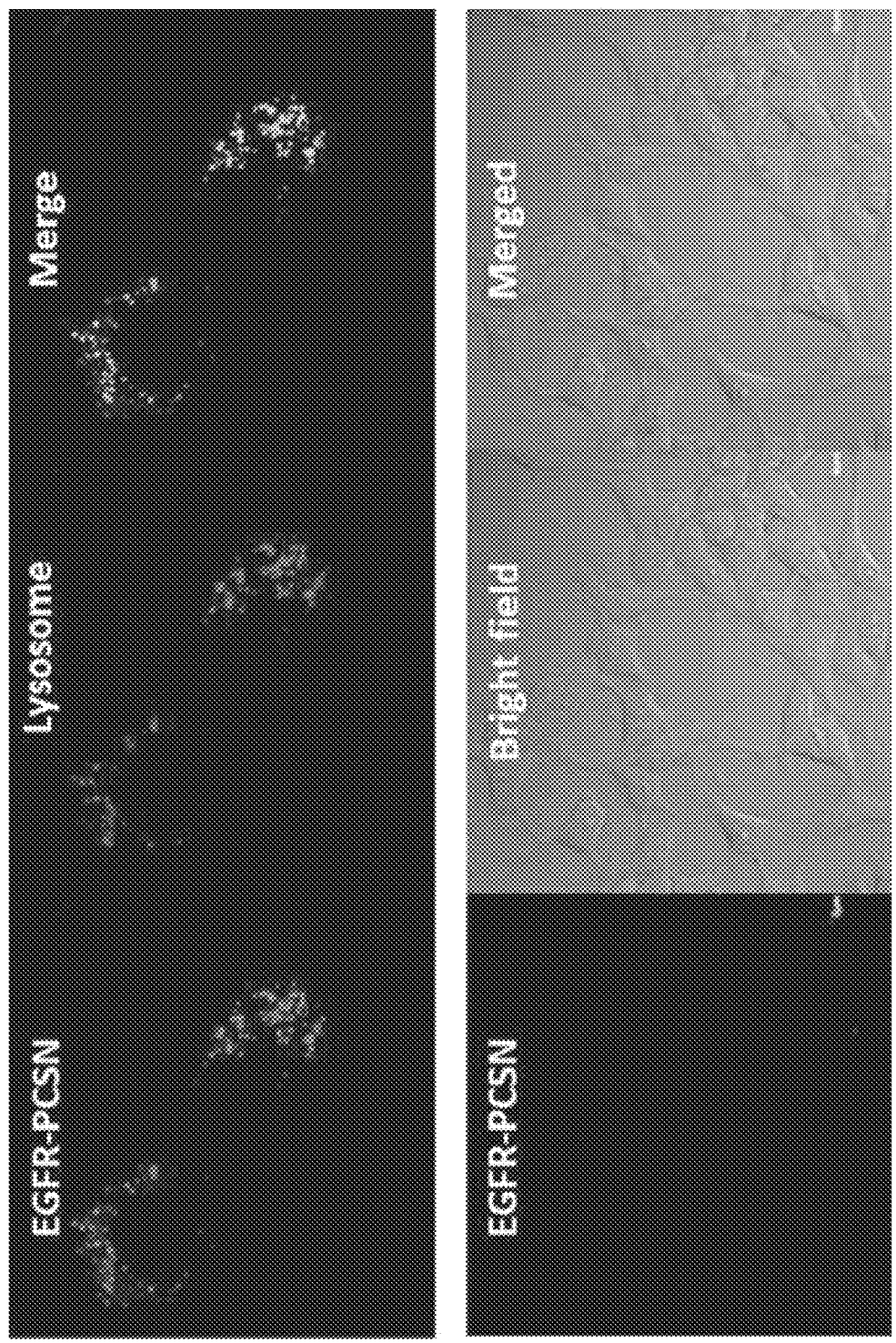

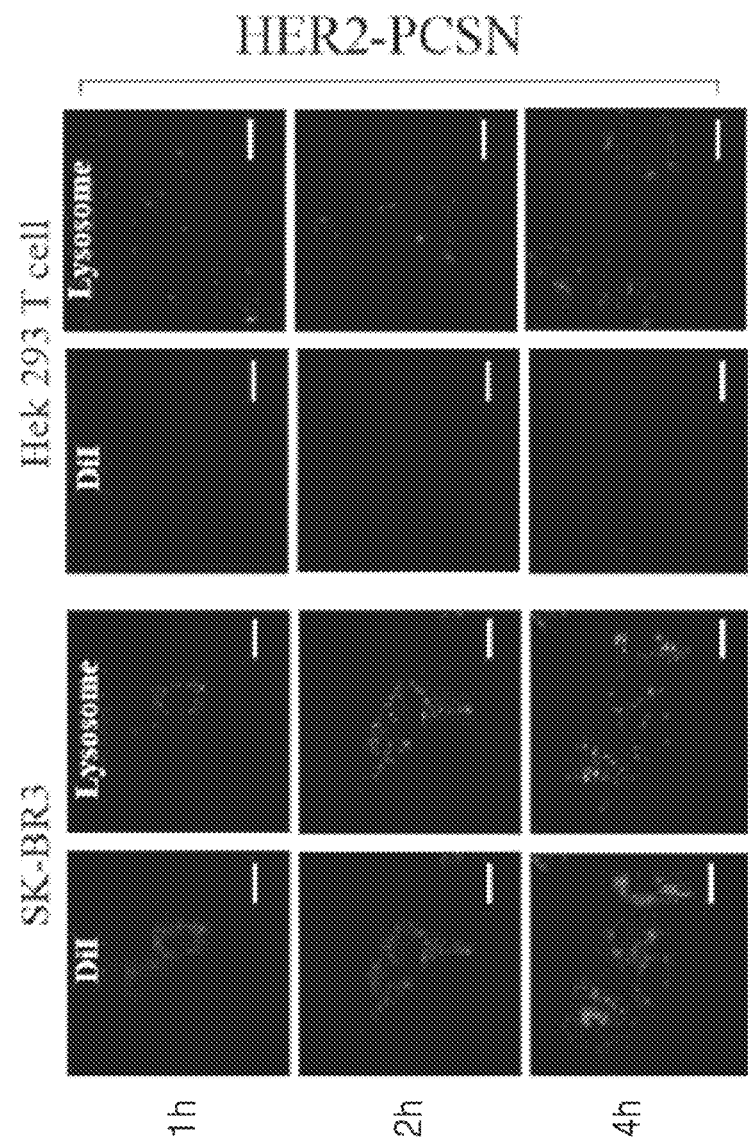

FUSION PROTEIN COMPRISING GLUTATHIONE-S-TRANSFERASE AND PROTEIN HAVING BINDING AFFINITY TARGET CELL OR TARGET PROTEIN, AND USE THEREOF

CROSS REFERENCE TO RELATED APPLICATIONS

This is the U.S. National Stage of International Application No. PCT/KR2018/014782, filed Nov. 28, 2018, which claims the benefit of Korean Patent Application No. 10-2017-0159936, filed Nov. 28, 2017, which is herein incorporated by reference in its entirety.

INCORPORATION OF SEQUENCE LISTING

The Sequence Listing is submitted as an ASCII text file, created on May 15, 2020, 2.78 KB, which is herein incorporated by reference.

TECHNICAL FIELD

The present disclosure relates to a fusion protein including glutathione-S-transferase and a protein having binding affinity for a target cell or a target protein, and use thereof as a drug delivery carrier and a pharmaceutical composition.

BACKGROUND ART

Nanoparticles are used as a useful tool in the fields of imaging devices, targeted therapeutics, etc., because they have excellent biological distribution and are able to control drug release. Generally, it is known that nanoparticles with a diameter of 200 nm may leak into blood vessels in the tumor periphery, and the leaked nanoparticles may continue to remain in the tumor tissue because of a low pressure due to a lack of lymphatic vessels around the tumor. This process is called an enhanced permeability and retention effect (EPR effect), through which permeability and retention of a drug delivery carrier may be improved.

Current commercially available nanoparticles may be represented by Abraxane and Doxil. However, there are limitations in that the nanoparticles exhibit different vascular permeability for different tumors, and when they are intravenously administered, nanoparticle clearance by the mononuclear phagocyte system (MPS) leads to accumulation thereof in reticuloendothelial organs such as liver and spleen. For this reason, targeted therapeutic agents to which nanoparticles are applied may have a reduced therapeutic effect, and may exhibit side effects due to toxicity of nanoparticles.

To overcome these disadvantages, a method of surrounding nanoparticles by poly(ethylene glycol)ylation (PEGylation) has been developed. When this method is used, there is an advantage in that the time for nanoparticles to circulate in the circulatory system in vivo may be prolonged, but on the contrary, the uptake by target cells may be reduced, and other cells than the target cells may be targeted through non-specific binding, which may also reduce therapeutic efficiency.

In using nanoparticles as a drug delivery system, a strategy to induce structural changes of nanoparticles has been proposed to enhance the EPR effect along with targeting ability for drug delivery. Specifically, attempts have been made to improve the targeting ability of drug delivery systems by inducing structural changes such as coating the surface of nanoparticles with antibodies, proteins, or peptides capable of binding to receptors overexpressed in cancer cells (Non-Patent Document 1). However, even with this method, tumor-targeting efficiency is not effectively increased. Rather, the method may provide a target ligand capable of more rapidly removing nanoparticles through an in vivo immune response by MPS, and thus there is a limitation in that a significant therapeutic effect may not be obtained in terms of the overall tumor therapeutic effect (Non-Patent Document 2).

Theoretically, when exposed to a physiological environment, the surface of nanoparticle is naturally surrounded by other biomolecules toward lowering the surface energy by combination of actions such as arrangement of water molecules according to the entropy, charge compensation of the particle surface, exposure of hydrophobic moiety, etc. At this time, various biomolecules are non-specifically adsorbed onto the surface of the nanoparticle, and this form is called protein corona. Protein corona is surrounded by other molecules, its natural molecular characteristics change, and target cell or organ-targeting ability and various biological functions expressed by nanoparticles are blocked (Non-Patent Document 3, and Non-Patent Document 4). For this reason, studies have been conducted to control the protein corona for application of nanoparticles as a targeted therapeutic agent at a clinical level (Non-Patent Document 5).

Accordingly, a method of controlling a protein corona after forming the protein corona on the surface of nanoparticle was developed during a process of preparing a nanoparticle-based targeted therapeutic agent (Non-Patent Document 6, Non-Patent Document 7, and Non-Patent Document 9). To this end, disclosed is a method of minimizing interaction with serum proteins by modifying the surface of nanoparticles with zwitterionic, PEG, or carbohydrate residues in order to avoid blocking of the targeting ability by the protein corona (Non-Patent Document 10, Non-Patent Document 11, Non-Patent Document 12, and Non-Patent Document 13). In addition, the protein corona may be controlled through circulation of a wanted protein in plasma by pre-coating nanoparticles with dysopsonic proteins. Accordingly, nanoparticles which are pre-coated with protein corona have increased stability at a colloidal state, and thus their circulation time may be maintained in the blood without clearance by MPS (Non-Patent Document 14, Non-Patent Document 15, Non-Patent Document 16, and Non-Patent Document 17). However, its clinical application also has limitations in that the targeting ability may be restricted even through the above method, and biochemical actions resulting from biological interactions between the nanoparticles and the proteins used in pre-coating are unknown.

DESCRIPTION OF EMBODIMENTS

Technical Problem

An aspect provides a fusion protein including glutathione-S-transferase (GST); and a protein having binding affinity for a target cell or a target protein.

Another aspect provides a drug delivery carrier including GST; a protein having binding affinity for a target cell or a target protein; and a drug bound with the GST.

Still another aspect provides a method of delivering a drug to an individual, the method including administering GST; a protein having binding affinity for a target cell or a target protein; and a drug bound with the GST to the individual in need thereof.

Still another aspect provides a pharmaceutical composition for preventing or treating cancer, the pharmaceutical composition including GST; a protein having binding affinity for a target cell or a target protein; and an anticancer agent bound with the GST.

Still another aspect provides a method of preventing or treating cancer, the method including administering a composition including GST; a protein having binding affinity for a target cell or a target protein; and an anticancer agent bound with the GST to an individual in need thereof.

Still another aspect provides use of a composition including GST; a protein having binding affinity for a target cell or a target protein; and an anticancer agent bound with the GST in preventing or treating cancer.

Solution to Problem

An aspect provides a fusion protein including glutathione-S-transferase (GST); and a protein having binding affinity for a target cell or a target protein.

The fusion protein may further include a linker which links the GST with the protein having binding affinity for a target cell or a target protein.

As used herein, the term "protein having binding affinity for a target cell or a target protein", "protein having ability to recognize a target cell", or "protein specifically binding to a target cell or a target protein" may refer to a protein specifically recognizing a receptor or a target protein of a cell or a protein specifically binding to a receptor or a target protein of a cell. Specifically, the protein specifically binding to a receptor or a target protein of a cell may be any one selected from the group consisting of an antibody, an antigen-binding fragment, an affibody, a diabody, and an aptamer.

As used herein, the term "affibody molecule" may refer to an antibody mimetic capable of binding to a specific target protein (receptor). Generally, the affibody molecule may consist of 20 to 150 amino acid residues, and may consist of 2 to 10 alpha helices. More specifically, the affibody molecule may include an anti-ErbB affibody molecule (ab31889), an HER2-specific affibody molecule (ZHER2: 342), an anti-EFFR affibody molecule (ZEGFR:2377), etc. Further, the affibody molecule includes, but is not limited to, all affibody molecules capable of recognizing a specific receptor or target protein of a cell. Examples of the target receptor or target protein which may be recognized by the affibody molecule may include amyloid beta peptide, synuclein (e.g., alpha-synuclein), apolipoprotein (e.g., apolipoprotein A1), complement factor (e.g., C5), carbonic anhydrase (e.g., CAIX), interleukin-2 receptor alpha chain (IL2RA; CD25), CD antigen on the cell surface (e.g., CD28), or c-Jun, Factor VIII, GP120, H-Ras, Her2, Her3, HPV16 E7, human islet amyloid polypeptide (IAPP), immunoglobulin A (IgA), IgE, IgM, interleukins (e.g., IL-1, IL-6, IL-8, IL-17), insulin, Staphylococcal protein A domain, Raf-1, light-oxygen-voltage-sensing domain (LOV domain), or RSV G protein. Information about the affibody is described in Stefan Stahl et al., Affibody Molecules in Biotechnological and Medical Applications, Trends in Biotechnology, August 2017, Vol 35, No 8, and the content of the publication disclosed as a reference herein are incorporated in the present disclosure.

The protein having binding affinity for a target cell or a target protein may specifically bind to receptor tyrosine kinases (RTKs). More specifically, the receptor tyrosine kinase may be any one selected from the group consisting of epidermal growth factor receptor, insulin receptor, platelet-derived growth factor receptor, vascular endothelial growth factor receptor, fibroblast growth factor receptor, cholecystokinin (CCK) receptor, neurotrophic factor (NGF) receptor, hepatocyte growth factor (HGF) receptor, ephrin (Eph) receptor, angiopoietin receptor, and related to receptor tyrosine kinase (RYK) receptor.

In a specific embodiment, the GST and the protein having binding affinity for a target cell or a target protein may be linked to each other via a linker. For example, the linker may be a polypeptide composed of any amino acids of 1 to 400, 1 to 200, or 2 to 200. The peptide linker may include Gly, Asn and Ser residues, and may also include neutral amino acids such as Thr and Ala. An amino acid sequence suitable for the peptide linker is known in the art. Further, to achieve appropriate functional moiety separation or to maintain necessary inter-moiety interaction, the copy number "n" may be adjusted by considering optimization of the linker. Other flexible linkers are known in the art, for example, G and S linkers including additional amino acid residues, such as T and A, to maintain flexibility, as well as polar amino acid residues to improve solubility. Therefore, in a specific embodiment, the linker may be a flexible linker including G, S, and/or T residue(s). The linker may have a formula selected from $(G_pS_s)_n$ and $(S_pG_s)_n$, wherein, each independently, p is an integer of 1 to 10, s is 0 or an integer of 0 to 10, p+s is an integer of 20 or less, and n is an integer of 1 to 20. More specifically, examples of the linker may include $(GGGGS)_n$ (SEQ ID NO: 2), $(SGGGG)_n$ (SEQ ID NO: 3), $(SRSSG)_n$ (SEQ ID NO: 4), $(SGSSC)_n$ (SEQ ID NO: 5), $(GKSSGSGSESKS)_n$ (SEQ ID NO: 6), $(RPPPPC)_n$ (SEQ ID NO: 7), $(SSPPPPC)_n$ (SEQ ID NO: 8), $(GST-SGSGKSSEGKG)_n$ (SEQ ID NO: 9), $(GST-SGSGKSSEGSGSTKG)_n$ (SEQ ID NO: 10), $(GST-SGSGKPGSGEGSTKG)_n$ (SEQ ID NO: 11), and $(EGKSSGSGSESKEF)_n$ (SEQ ID NO: 12), wherein n is an integer of 1 to 20, or 1 to 10.

Another aspect provides a polynucleotide encoding the fusion protein.

The term "polynucleotide" means a polymer of deoxyribonucleotides or ribonucleotides that exist in single-stranded or double-stranded form. The polynucleotide encompasses RNA genomic sequences, DNA (gDNA and cDNA) and RNA sequences transcribed therefrom, and includes natural polynucleotides as well as analogs thereof in which sugar or base moieties are modified, unless otherwise specified. In a specific embodiment, the polynucleotide is a single-stranded polynucleotide.

Still another aspect provides a vector including the polynucleotide.

As used herein, the term "vector", which is a vector capable of expressing a target protein in an appropriate host cell, refers to a gene construct including a regulatory element operably linked to express a gene insert. The vector according to one embodiment may include expression control elements such as a promoter, an operator, a start codon, a stop codon, a polyadenylation signal, and/or an enhancer, and the promoter of the vector may be constitutive or inducible. Further, the vector may be an expression vector capable of stably expressing the fusion protein in a host cell. The expression vector may be those commonly used to express foreign proteins in plants, animals, or microorganisms in the art. The recombinant vector may be constructed by various methods known in the art. For example, the vector may include a selectable marker for selecting a host cell containing the vector, and in the case of a replicable vector, it may include an origin of replication. In addition, the vector may be self-replicable or may be introduced into a host DNA, and the vector may be selected from the group consisting of a plasmid, lentivirus, adenovirus, adeno-associated virus, retrovirus, herpes simplex virus, and vaccinia virus.

The vector includes a promoter operable in animal cells, e.g., mammalian cells. An appropriate promoter according to one embodiment includes promoters derived from mammalian viruses and promoters derived from genomes of mammalian cells, and may include, for example, a cytomegalovirus (CMV) promoter, a U6 promoter and an H1 promoter, a long terminal repeat (LTR) promoter of murine leukemia virus (MLV), an adenovirus early promoter, an adenovirus late promoter, a vaccinia virus 7.5K promoter, a SV40 promoter, a tk promoter of HSV, an RSV promoter, an EF1 alpha promoter, a metallothionein promoter, a beta-actin promoter, a promoter of human IL-2 gene, a promoter of human IFN gene, a promoter of human IL-4 gene, a promoter of human lymphotoxin gene, a promoter of human GM-CSF gene, a human phosphoglycerate kinase (PGK) promoter, a mouse phosphoglycerate kinase (PGK) promoter, and a survivin promoter.

In addition, in the vector, the above-described fusion protein may be operably linked to the promoter. As used herein, the term "operably linked" refers to a functional linkage between a nucleic acid expression control sequence (e.g., a promoter, a signal sequence, or an array of transcription factor binding sites) and another nucleic acid sequence, wherein the expression control sequence regulates transcription and/or translation of another nucleic acid sequence.

Still another aspect provides a host cell including the fusion protein, the polynucleotide, or the vector.

The cells, e.g., eukaryotic cells, may be yeasts, fungi, protozoa, plants, higher plants, insects, amphibian cells, or mammalian cells such as CHO, HeLa, HEK293, and COS-1. For example, the cells may be cultured cells (in vitro), transplanted cells (graft cells), and primary culture cell (in vitro and ex vivo) and in vivo cells, and may also be mammalian cells including human cells, which are usually used in the art. Further, the organism may be a yeast, a fungus, a protozoa, a plant, a higher plant, an insect, an amphibian, or a mammal. Further, the cells may be animal cells or plant cells.

Still another aspect provides a drug delivery carrier including GST; a protein having binding affinity for a target cell or a target protein; and a drug bound with the GST.

Still another aspect provides a method of delivering a drug to an individual, the method including administering GST; a protein having binding affinity for a target cell or a target protein; and a drug bound with the GST to the individual in need thereof.

The fusion protein including the GST and the protein having binding affinity for a target cell or a target protein is the same as described above.

In a specific embodiment, the binding of the GST and the drug may occur via glutathione (GSH). In other words, the drug may be a drug to which GSH is bound. The GSH functions as a binding site of GST to link the drug with the GST.

A kind of a pharmaceutical active ingredient which may be delivered to an individual using the drug delivery carrier may include an anticancer agent, a contrast agent (dye), a hormonal agent, an anti-hormonal agent, a vitamin agent, a calcium agent, a mineral agent, a sugar agent, an organic acid agent, a protein amino acid agent, an antidote agent, an enzyme agent, a metabolic agent, a diabetes combination agent, a tissue rejuvenation drug, a chlorophyll preparation, a pigment preparation, a tumor drug, a tumor therapeutic agent, a radiopharmaceutical preparation, a tissue cell diagnostic agent, a tissue cell therapeutic agent, an antibiotic preparation, an antiviral agent, a complex antibiotics, a chemotherapeutic agent, a vaccine, a toxin, a toxoid, an antitoxin, leptospira serum, a blood product, a biological product, an analgesics, an immunogenic molecule, an antihistamine agent, an allergic drug, a non-specific immunogen preparation, an anesthetics, a stimulant, a psychotropic agent, a small molecular compound, a nucleic acid, an aptamer, an antisense nucleic acid, an oligonucleotide, a peptide, siRNA, micro RNA, etc.

Further, the anticancer agent may include camptothecin, doxorubicin, cisplatin, verapamil, fluorouracil, oxaliplatin, daunorubicin, irinotecan, topotecan, paclitaxel, carboplatin, gemcitabine, methotrexalte, docetaxel, acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus Calmette-Guérin (BCG), Baker's Antifol, beta-2-deoxythioguanosine, bisantrene HCl, bleomycin sulfate, busulfan, buthionine sulfoximine, BWA 773U82, BW 502U83/HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, Corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alpha, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, a methanol extract of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, pharmaceutically acceptable salts thereof, and mixtures thereof, etc.

In another specific embodiment, the drug may be drug-loaded nanoparticles or nanoparticles capable of loading the drug. The nanoparticles may be any nanoparticles without limitation, as long as they may be applied as a drug delivery carrier according to a known technology. Specifically, the nanoparticles may be any one selected from the group consisting of mesoporous silica nanoparticles (MSN), gold nanoparticles, magnetic nanoparticles, nucleic acid-metal organic framework nanoparticles, and polymer nanoparticles. Further, the nanoparticles may be nanoparticles to which GSH is bound. Therefore, the nanoparticles may bind with the fusion protein including GST. Further, the nanoparticles may specifically load an anticancer chemotherapeutic agent.

In this regard, a protein that specifically recognizes cancer tissue cells of which death is induced by the corresponding anticancer chemotherapeutic agent may be interpreted as being a protein having ability to recognize the target cells.

Still another aspect provides a pharmaceutical composition for preventing or treating cancer, the pharmaceutical composition including GST; a protein having binding affinity for a target cell or a target protein; and an anticancer agent bound with the GST.

Still another aspect provides a method of preventing or treating cancer, the method including administering a composition including GST; a protein having binding affinity for a target cell or a target protein; and an anticancer agent bound with the GST to an individual in need thereof.

Still another aspect provides use of a composition including GST; a protein having binding affinity for a target cell or a target protein; and an anticancer agent bound with the GST in preventing or treating cancer.

The GST, the protein having binding affinity for a target cell or a target protein, and the anticancer agent bound with the GST are the same as described above.

The terms "subject", "individual", and "patient" are used interchangeably herein to designate vertebrates, specifically mammals, and more specifically humans. The mammals include, but are not limited to, murines, monkeys, humans, farm animals, sport animals, and pets. Tissues and cells of a biological entity obtained in vivo or cultured in vitro, and progeny thereof are also encompassed.

The term "therapeutic agent" or "pharmaceutical composition" refers to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder, or illness; and generally counteracting a disease, symptom, disorder or pathological condition.

As used herein, "treatment" or "treating," or "palliating" or "ameliorating" are used interchangeably. These terms refer to a method of obtaining beneficial or wanted results including, but not limited to, a therapeutic benefit and/or a prophylactic benefit. Therapeutic benefit means any therapeutically relevant improvement in or effect on one or more diseases, illnesses, or symptoms under treatment. For prophylactic benefit, the compositions may be administered to a subject at risk of developing a particular disease, illness, or symptom, or to a subject reporting one or more of the physiological symptoms of a disease, even though the disease, illness, or symptom may not have yet been manifested.

The term "effective amount" or "therapeutically effective amount" refers to the amount of an agent that is sufficient to cause beneficial or wanted results. The therapeutically effective amount may vary depending upon one or more of a subject and disease conditions being treated, the subject's weight and age, severity of the disease conditions, administration manner, etc., which may be readily determined by one of ordinary skill in the art. The term is also applied to a dose that will provide an image for detection by any one of the imaging methods described herein. The specific dose may vary depending on one or more of a particular agent chosen, a dosing regimen to be followed, whether it is administered in combination with other compounds, timing of administration, a tissue to be imaged, and a physical delivery system in which it is carried.

The cancer may be lung cancer (e.g., non-small cell lung cancer), pancreatic cancer, stomach cancer, liver cancer, colon cancer, brain cancer, breast cancer, thyroid cancer, bladder cancer, esophageal cancer, or uterine cancer. In addition, the cancer may be any one or more selected from the group consisting of stomach cancer, breast cancer, lung cancer, liver cancer, esophageal cancer, and prostate cancer having resistance to anticancer agents (e.g., multidrug resistance).

The pharmaceutical composition may be parenterally administered during clinical administration, and may be used in the form of a general pharmaceutical formulation. Parenteral administration may refer to administration via an administration route other than an oral route, such as rectal, intravenous, peritoneal, intramuscular, intraarterial, transdermal, nasal, inhalation, ocular and subcutaneous routes. When the pharmaceutical composition of the present disclosure is used as a medical product, one or more active ingredients exhibiting the same or similar function may be further included.

Upon formulating the pharmaceutical composition, it is prepared by using a commonly used diluent or excipient, such as a filler, an extender, a binder, a wetting agent, a disintegrating agent, a surfactant, etc. Formulations for parenteral administration include sterile aqueous solutions, non-aqueous solvents, suspensions, emulsions, lyophilized preparations, and suppositories. As the non-aqueous solvent and the suspension solvent, propylene glycol, polyethylene glycol, vegetable oil such as olive oil, injectable ester such as ethyl oleate, etc. may be used. As a base for suppositories, Witepsol, Macrogol, Tween 61, cacao butter, laurin butter, glycerogelatin, etc. may be used.

Further, the pharmaceutical composition may be used in combination with various carriers allowed as pharmaceutical agents such as physiological saline or organic solvents, and to increase stability or absorption, carbohydrates such as glucose, sucrose, or dextran, antioxidants such as ascorbic acid or glutathione, chelating agents, low molecular proteins, or other stabilizers may be used as pharmaceutical agents.

The effective dose of the pharmaceutical composition may be 0.01 mg/kg to 100 mg/kg, specifically, 0.1 mg/kg to 10 mg/kg, and may be administered once to three times a day.

Still another aspect provides a nanoparticle with a protein corona shield (PCSN) including the following components:
a) a nanoparticle capable of loading a drug; b) a fusion protein including GST, which is bound to the surface of the nanoparticle.

Further, the present disclosure provides a nanoparticle drug delivery carrier with a protein corona shield, in which a drug is loaded in the nanoparticle.

Further, the present disclosure provides a method of preparing a nanoparticle drug delivery carrier with a protein corona shield, the method including the following i) to iii):
i) binding a linker (e.g., GSH) to the surface of nanoparticle; ii) loading a drug inside or on the surface of the nanoparticle bound with the linker in i); and iii) coating the surface of the drug-loaded nanoparticle in ii) with GST fusion protein to form the protein corona shield (PCS).

In the nanoparticle, PCS is first formed by pre-coating the surface with the fusion protein, and therefore, the corona shield surrounded by serum proteins in the body environment is not formed. As a result, the nanoparticles may avoid immune responses by macrophages, thereby having a significant stealth effect. Accordingly, nanoparticles (PCSN) with PCS may not only sustain in vivo retention time but also have improved ability to target a target cell, thereby being effectively delivered to the target cell. Thus, the nanoparticles may be usefully applied as a targeted therapeutic agent.

Advantageous Effects of Disclosure

A fusion protein according to one aspect and a drug delivery carrier including the same may not only sustain in vivo retention time but also improve ability to target a target cell, thereby being effectively delivered to the target cell. Accordingly, they may be usefully applied to a targeted therapeutic agent.

BRIEF DESCRIPTION OF DRAWINGS

FIG. 1 shows a process of preparing a nanoparticle with a protein corona shield (PCSN) in the present disclosure;

FIG. 1A is an illustration of a strategy for preparing PCSN of the present disclosure to overcome a limitation that a drug delivery carrier does not exhibit a significant drug delivery ability with respect to a target cell in vivo, and FIG. 1B is an illustration of a process of preparing PCSN in which a corona shield is formed with a GST-Afb fusion protein;

FIG. 2 shows an expression process of a shield fusion protein used in PCSN;

FIGS. 2A and 2B show a process of purifying GST-HER2 and GST-EGFR fusion proteins after expressing them, and FIG. 2C shows results of examining molecular weights of the expressed and purified fusion proteins;

FIG. 3 shows results of examining cytotoxicity and cell targeting ability of a GST-Afb fusion protein;

FIG. 3A shows results of confirming that the GST-Afb fusion protein did not reduce cell viability of Afb target cells, and FIG. 3B shows results of confirming that the GST-Afb fusion protein exhibited cell targeting ability with respect to Afb target cells;

FIG. 4 shows results of preparing a drug delivery carrier with a protein corona shield (PCN);

FIG. 4A shows results of examining surface charges of PCSN and controls, FIG. 4B shows results of FTIR analysis to examine reactive groups distributed on the surfaces of PCSN and MMSN, FIG. 4C shows results of observing shapes of the prepared PCSN and MMSN, and FIG. 4D shows results of examining storage stability of HER2-PCSN;

FIG. 5 shows results of examining quantity of a protein forming a protein corona on the surface of PCSN;

FIG. 5A shows SDS-PAGE results of the protein separated from the surface of nanoparticles stored in 55% serum for 4 hr, and FIG. 5B shows results of quantifying the SDS-PAGE separation results;

FIG. 6 shows results of proteomic analysis of serum proteins bound to the surfaces of nanoparticles;

FIG. 6A shows results of dividing serum proteins bound to the surfaces of MMSN, PMSN, and PCSN into three groups according to their binding patterns, FIGS. 6B to 6D show results of dividing the serum proteins bound to the surfaces of the nanoparticles according to their molecular weight, isoelectric point, and function, and FIG. 6E shows results of classifying the binding patterns of protein groups subdivided according to their function;

FIG. 7 shows results of examining tumor cell targeting ability of PCSN;

FIGS. 7A and 7B show results of intracellular localization of CPT-loaded HER2-PCSN and EGFR-PCSN after treatment of SK-BR3 cells or MDA-MB-468 cells therewith, and FIG. 7C shows results of flow cytometry of Hek293T cells, SK-BR3 cells, or MDA-MB-468 cells after treatment with Dil-loaded HER2-PCSN or EGFR-PCSN;

FIG. 8 shows results of evaluating uptake ability to deliver a drug from PCSN into tumor cells;

FIG. 8A shows images of MDA-MB-468 cells after treatment with CPT-loaded EGFR-PCSN, and FIG. 8B shows images of Hek297T cells after treatment therewith;

FIG. 9 shows results of examining cytotoxicity of PCSN with respect to target cells;

FIG. 9A shows cell viability of SK-BR3 cells or Hek297T cells after treatment with CPT-loaded HER2-PCSN, and FIG. 9B shows cell viability of MDA-MB-468 cells or Hek297T cells after treatment with CPT-loaded EGFR-PCSN;

FIG. 10 shows results of examining cell targeting ability and cytotoxicity of doxorubicin (DOX)-loaded PCSN;

FIGS. 10A and 10B show images of SK-BR3 cells or MDA-MB-468 cells after treatment with DOX-loaded HER2-PCSN or EGFR-PCSN, and FIGS. 10C and 10D show cell viability of SK-BR3 cells or MDA-MB-468 cells after treatment with DOX-loaded HER2-PCSN or EGFR-PCSN;

FIG. 11 is an illustration of a stealth effect of nanoparticles with a GST-Afb shield with respect to macrophages;

FIG. 11A is an illustration showing that PCSN avoids immune responses of macrophage by blocking formation of a corona shield surrounded by serum proteins, and FIG. 11B is an illustration showing a drug delivery process of PCSN after being stored in 55% serum in order to examine its stealth effect;

FIG. 12 shows results of examining PCSN phagocytosis of macrophages and cytotoxicity of PCSN with respect to macrophages;

FIGS. 12A and FIG. 12B show cell fluorescence images over time when MDA-MB-468 cells, SK-BR3 cells, or Hek293T cells were treated with Dil-loaded EGFR-PCSN and HER2-PCSN, FIG. 12C shows cell fluorescence images at 6 hr after SK-BR3 cells were treated with Dil-loaded PMSN or HER2-PCSN, FIG. 12D shows results of flow cytometry of the cells in the cell fluorescence images observed above, and FIG. 12E shows results of examining cell viability of macrophage RAW 264.7 after treatment with CPT-loaded HER2-PCSN;

FIG. 13 shows results of examining tumor cell targeting ability of PCSN stored in vivo environment;

FIG. 13A shows images of Hek297T cells or SK-BR3 cells after treatment with Dil-loaded HER2-PCSN which was stored in 55% serum for 4 hr, FIG. 13B shows images of MBA-MD-468 cells after treatment with CPT-loaded EGFR-PCSN which was stored in 55% serum, and FIG. 13C shows cell viability of SK-BR3 cells or Hek297T cells after treatment with CPT-loaded HER2-PCSN which was stored in 55% serum;

FIG. 14 shows results of examining in vivo anticancer effects of PCSN;

MODE OF DISCLOSURE

Figure 1A:
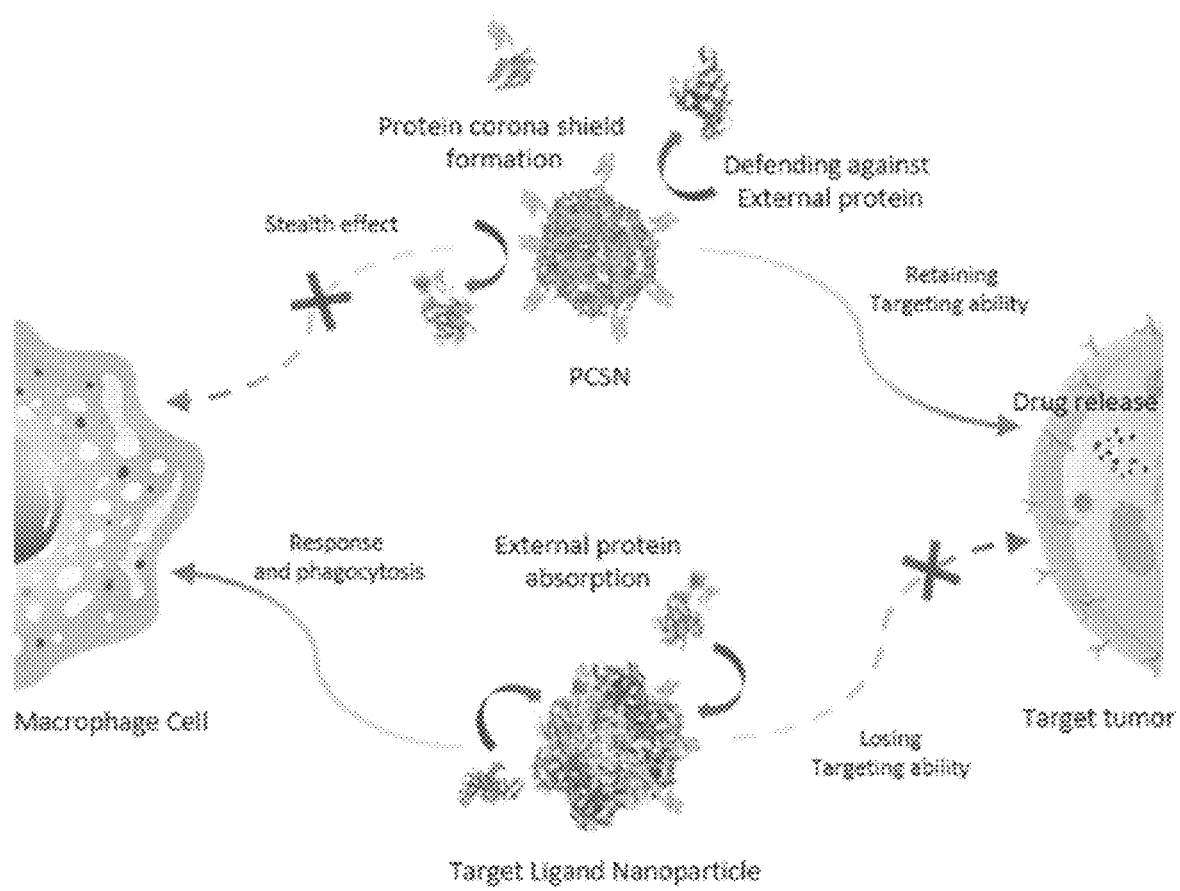

Hereinafter, the present disclosure will be described in more detail with reference to exemplary embodiments. However, these exemplary embodiments are provided only for illustrating the present disclosure, and it is apparent to those skilled in the art that the scope of the present disclosure is not limited by these exemplary embodiments.

Example 1. Expression of Shield Fusion Protein Used for Nanoparticles with Protein Corona Shield <1-1> Preparation of Fusion Protein of Affibody and Glutathione-S-Transferase (GST)

In the present disclosure, a drug delivery carrier having improved stability and targeting ability even in vivo environment was prepared by forming a protein corona shield on the surface of nanoparticles to be used as a drug delivery carrier. To this end, a fusion protein which may constitute the protein corona shield was first prepared. The fusion protein was expressed in such a form that GST were bound with affibody (Afb) capable of specifically binding to receptors of cancer cell surface.

Specifically, in the present disclosure, HER2 Afb specifically binding to HER2 and EGFR Afb specifically binding to EGFR were used as the Afb. A gene encoding an extra linker domain (SEQ ID NO: 1: GGGLVPRGSGGGCGGGGTGGGSGGG) was linked to the end of each gene encoding HER2 Afb or EGFR Afb, which was then inserted into a pETduet plasmid. For GST overexpression, a GST-encoding gene which was designed to link a 6×His tag to the N-terminus of GST was inserted into the pETduet plasmid, thereby constructing a plasmid for overexpressing the fusion protein (GST-Afb) in which Afb and GST were linked to each other via the linker. PCR and DNA sequencing analysis were performed to examine whether the GST-Afb encoding sequence was normally inserted into the constructed plasmid. Thereafter, the constructed plasmid was transformed into an *E. coli* BL21(DE3) strain, followed by incubation. The strain was treated with IPTG and incubated at 30° C. for 16 hr to induce GST-Afb overexpression. *E. coli* cells of which overexpression was induced was centrifuged at 5000×g and 4° C. for 10 min to obtain precipitated cells, which were then suspended in a phosphate buffer solution (50 mM sodium phosphate and 100 mM sodium chloride, pH 6.5). The cell suspension was treated with lysozyme, incubated at room temperature for 20 min, and then sonicated for a total of 10 min with 30-sec sonication and 1-min interval. After sonication, centrifugation was carried out at 12000×g and 4° C. for 1 hr to obtain a supernatant as a GST-Afb-containing fraction. The supernatant was purified by immobilized metal affinity chromatography (1 mL HisTrap FF column, GE HealthCare) using FPLC to isolate GST-Afb. The isolated GST-Afb (GST-HER2 Afb and GST-EGFR Afb) were concentrated by dialysis in PBS (pH 7.4) overnight. The concentrated GST-HER2 Afb and GST-EGFR Afb were subjected to SDS-PAGE analysis and electrospray ionization time-of-light mass spectrometry (ESI-TOF MS) analysis to analyze purities and molecular weights of the isolated proteins.

As a result, as shown in FIG. 2, expression and molecular weights of GST-HER2 Afb and GST-EGFR Afb were confirmed. It was confirmed that when the fraction isolated by the immobilized metal affinity chromatography was analyzed by SDS, GST-HER2 Afb and GST-EGFR Afb were purified with purity of 99.0% or more, respectively (FIGS. 2A and 2B), and when their molecular weights were analyzed, the molecular weight of GST-HER2 Afb was about 36.3 kDa and the molecular weight of GST-EGFR Afb was about 36.14 kDa (FIG. 2C).

<1-2> Examination of Cytotoxicity and Cell Targeting Ability of GST-Afb Fusion Protein To confirm whether the GST-Afb fusion protein expressed in the present disclosure may be applied to a protein corona shield (PCS) in a drug delivery carrier, cytotoxicity and cellular uptake were examined.

In detail, to examine cytotoxicity of GST-HER2 Afb, SK-BR-3 cell which is a human breast cancer cell line was first prepared. The prepared SK-BR-3 cells were cultured in a DMEM medium (11995065, Invitrogen, S. Korea). To the medium, 10% fetal bovine serum (FBS), 100 µg/ml streptomycin, and 100 U/ml penicillin were added, and the medium was replaced once daily during the culture period. The culture environment was maintained in a 5% $CO_2$ incubator at 37° C. After seeding, when the cells proliferated to reach 85% confluence, the adhered cells were separated and used for experiments. SK-BR-3 cells were separated and seeded in a 96-well plate (Thermo Scientific Inc. Korea) at a density of $5 \times 10^3$ cells/well, and incubated in a 5% $CO_2$ incubator at 37° C. for 24 hr. Thereafter, SK-BR-3 cells were treated with GST-HER2 Afb obtained in Example <1-1> at a concentration of 0.3 µM to 10 µM, and further incubated for 24 hr. After completing incubation, cell viability was examined using an alamar blue dye (DAL 2015, Invitrogen, Korea). To examine cell viability, an excitation wavelength for the fluorescence dye was set at 565 nm, and a monitoring emission was set at 590 nm, and then fluorescence was analyzed using a fluorescence plate reader (Tecan Infinite Series, Germany). Further, GST in GST-HER2 Afb was labeled with fluorescein-5-maleimide (F5M) to examine localization of intracellular uptaken GST-HER2 Afb. As a negative control, a normal epithelial cell line MCF-10A was used to examine cell viability and cellular uptake in the same manner.

In addition, to monitor interactions between GSH in GST-Afb and a target receptor in real time, a quartz crystal microbalance (QCM) and surface plasmon resonance (SPR) analysis were performed.

Figure 3A:
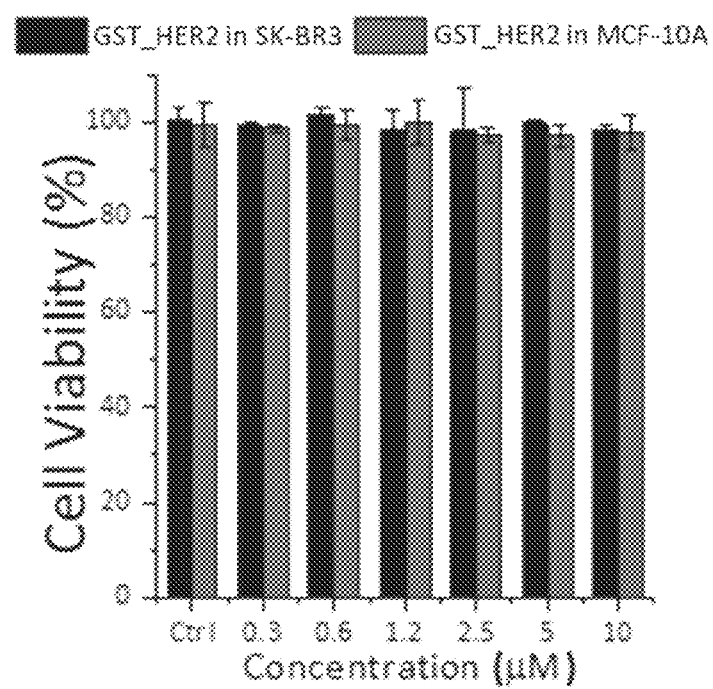
Figure 3B:
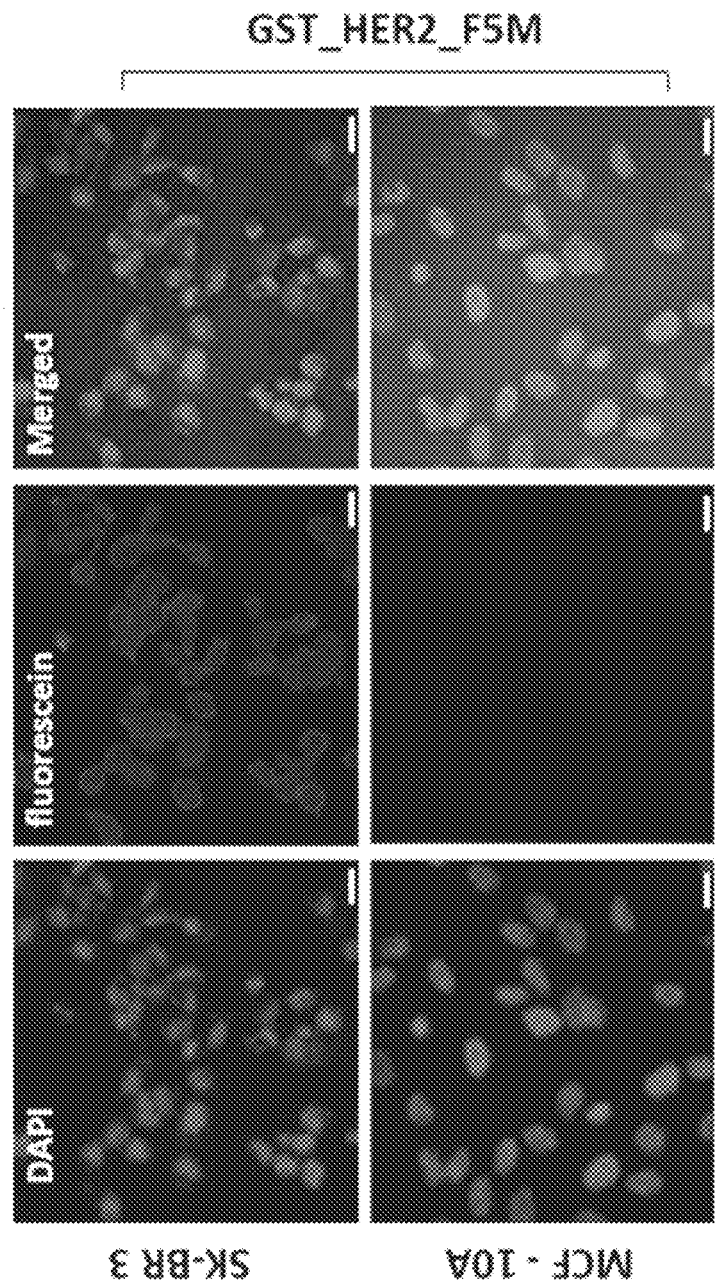

As a result, as shown in FIG. 3, it was confirmed that GST-HER2 Afb did not exhibit cytotoxicity against the cells, but may be specifically absorbed by cancer cells. When SK-BR-3 cells and MCF-10A cells were cultured by treatment with GST-HER2 Afb, cell death was not observed regardless of treatment concentration, indicating no cytotoxicity of GST-Afb (FIG. 3A), whereas GST-HER2 Afb exhibited binding affinity only with respect to the breast cancer cell line SK-BR-3, indicating that GST-Afb exhibits cancer cell-specific targeting ability (FIG. 3B). These results confirmed that the GST-Afb fusion protein expressed to be used as the protein corona shield in the present disclosure may exhibit no cytotoxicity against normal cells and may exhibit targeting ability with respect to cancer cells.

Example 2. Preparation of Drug Delivery Carrier with Protein Corona Shield (PCN)

<2-1> Preparation of Mesoporous Silica Nanoparticles

As a basic structure of the drug delivery carrier, mesoporous silica nanoparticles (MSNs) were prepared. MSNs were divided into two types. MSNs having a diameter of 100 nm or less and MSNs having a diameter of 50 nm or less were prepared.

First, to prepare MSNs having a diameter of 100 nm or less, 1.0 g of cetyltrimethylammonium bromide (CTAB) was dissolved in 480 g of 0.015 M NaOH solution under stirring at 80° C. When CTAB was completely dissolved, 4.7 g of TEOS as a surfactant was added and further stirred at 800 rpm for 2 hr. When the stirred solution appeared in a white solid phase, it was filtered using a vacuum filter, washed with deionized water (DI water), and dried in air at 70° C. to obtain a dry product. The obtained dry product was homogenized using an agate mortar and then calcined at 550° C. for 5 hr to finally obtain MSNs.

Meanwhile, to prepare MSNs having a diameter of 50 nm or less, 1.53 g of CTAB and 0.3 g of tetraethylammonium hydroxide (TEAH) were added to 100 g of DI water, and then dissolved under stirring at 80° C. for 1 hr. When CTAB and TEAH were completely dissolved, 14.45 g of TEOS was added thereto, and further stirred at 800 rpm for 2 hr. When the stirred solution appeared in a white solid phase, it was filtered using a vacuum filter, washed with DI water, and dried in air at 70° C. to obtain a dry product. The obtained dry product was homogenized using an agate mortar and then calcined at 550° C. for 5 hr to finally obtain MSNs.

<2-2> Preparation of PEGylated MSNs

In the existing technology, when nanoparticles are used as a drug delivery carrier, MSNs of which surface is PEGylated is used. Therefore, in the present disclosure, PEGylated MSNs (PMSN) prepared by PEGylation of the surface of MSNs was prepared to be used as a control.

In detail, 5 mg of a dye or a drug was loaded on MSNs prepared in Example <2-1>, and then MSNs were dispersed in 1 ml of DI water containing 10 mg of PEG-PDS polymer, followed by stirring at room temperature for 12 hr. Thereafter, to crosslink the polymer as a MSN shield, DTT was added at a final concentration of 50 mol % to a PDS group under stirring at room temperature over 3 hr to allow crosslinking. When 3-hr stirring was completed, drug-loaded MSNs surrounded by PEG polymer were collected by centrifugation, and washed with phosphate buffer at pH 7.4 (10 mM) and DI water a total of three times. During washing, the supernatant was separately collected, and then a by-product (pyridothione) released during polymer crosslinking through a thiol-disulfide exchange reaction and any removed drugs were measured using UV-Visible spectrometry.

<2-3> Preparation of Nanoparticle of which Surface is Bound with GST

As a process of preparing nanoparticles with a protein corona shield of the present disclosure, nanoparticles (GSH-modified particles, MMSNs), of which surface was bound with glutathione (GSH) by thiol-ene click chemistry, were prepared.

In detail, 100 mg of MSNs prepared in Example <2-1> and 1 ml of 3-(trimethoxysilyl) propyl acrylate were mixed in 18 ml of toluene. The mixed solution was allowed to react under stirring at 60° C. for 24 hr. After reaction, MSNs were washed with ethanol and DI water, and then added to 16 ml of DMF to prepare MSNs. GSH for shield formation was prepared by dissolving 100 mg of GSH in 2 ml of DI water. Thereafter, the prepared MSN-containing solution and GSH aqueous solution were mixed and 40 μl of pyridine was added thereto, and stirred by vortexing. After stirring, the mixed solution was left at room temperature for 72 hr and allowed to react. After completion of the reaction, nanoparticles were washed with ethanol three times, and vacuum-dried at room temperature to finally obtain nanoparticles (MMSNs), of which surface was bound with GSH.

<2-4> Preparation of Nanoparticles with GST-Afb Protein Corona Shield

Figure 1B:
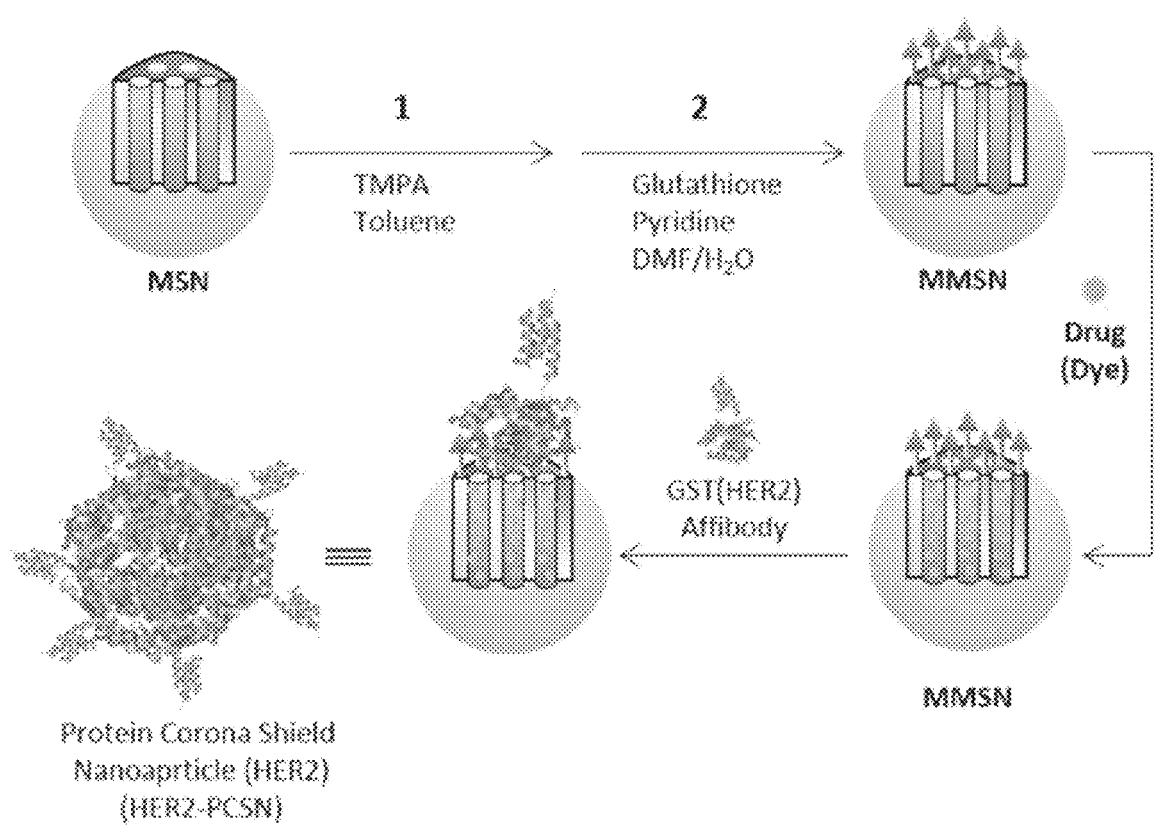
Figure 2A:
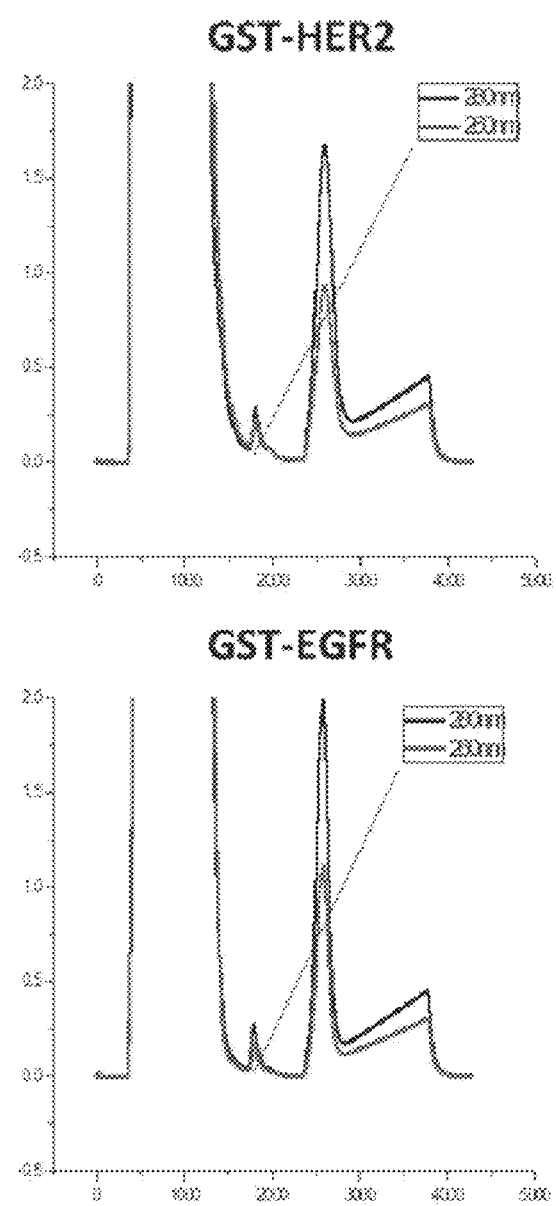
Figure 2B:
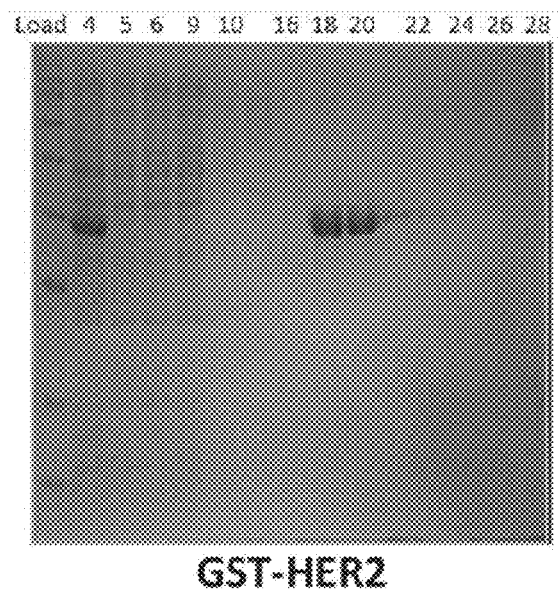
Figure 2B:
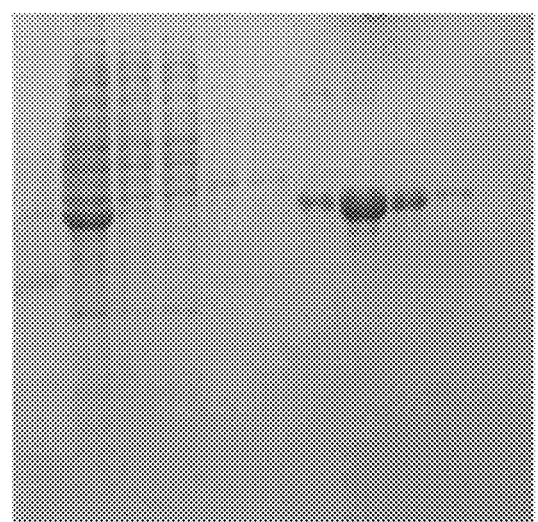
Figure 2C:
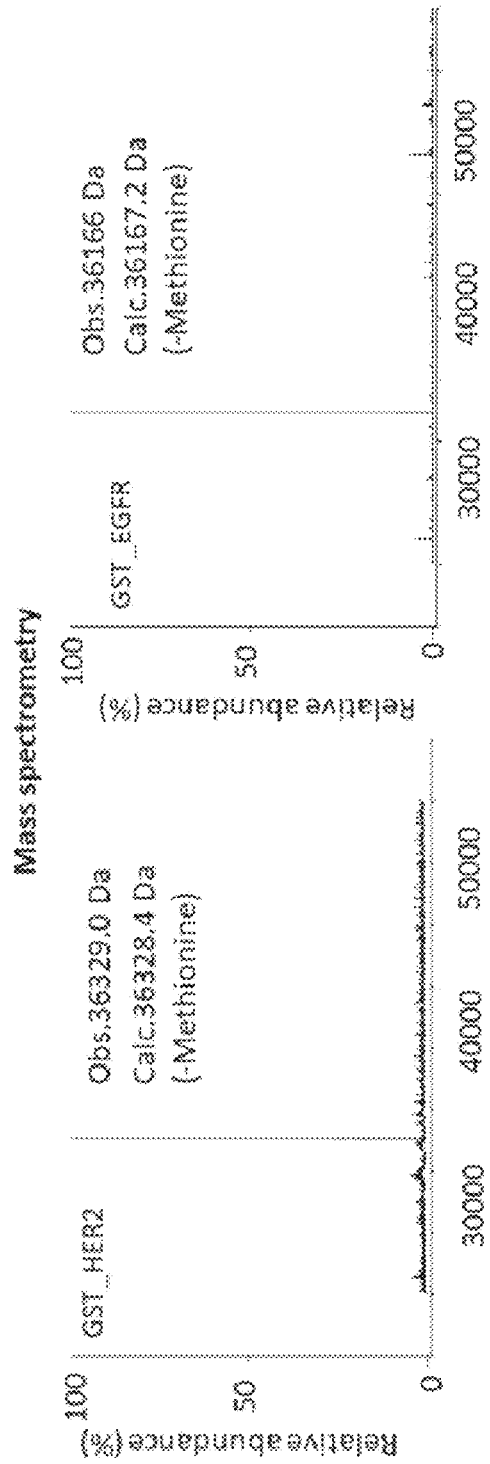

To prepare protein corona shield nanoparticles (PCSNs) to be used as a drug delivery carrier in the present disclosure, nanoparticles to which GST-Afb was applied as the protein corona shield were prepared. MSNs are used as a delivery carrier capable of loading a material via a chemical functional group inside thereof or on the surface thereof. Therefore, in the present disclosure, GSH was bound onto the surface of MSN to prepare MMSNs, and then a protein corona shield was formed thereto via GST, thereby preparing PCSNs through a process of FIG. 1B.

In detail, each 1 mg of GST-HER2 Afb or GST-EGFR Afb purified and prepared in Example <1-1> was dissolved in 2 ml of PBS (pH 7.4) to prepare a protein solution. Further, 1 mg of MMSN prepared in Example <2-3> was added to 3 ml of PBS. Thereafter, the MMSN solution was slowly added to and mixed with the GST-Afb protein solution under stirring at 4° C. These two solutions were fully mixed, and then further stirred at 4° C. for 1 hr. After stirring, centrifugation was performed at 5000 rpm to remove unbound residual proteins, followed by washing with PBS. Finally, PCSNs were collected and stored in 5 ml of PBS.

Example 3. Physicochemical Characterization of Drug Delivery Carrier with Protein Corona Shield (PCN)

<3-1> Analysis of Surface Charge of Protein Corona Shield Nanoparticles (PCSNs)

To examine a surface charge of PCSNs prepared in the present disclosure, a zeta-potential of nanoparticles dispersed in physiological pH environment was measured to examine the surface charge of the drug delivery carrier. To compare this, surface charges of GST-Afb prepared in Example <1-1> and MSNs, PMSNs, MMSNs, and PCSNs which are drug delivery carriers prepared in [Example 2] were examined.

Figure 4A:
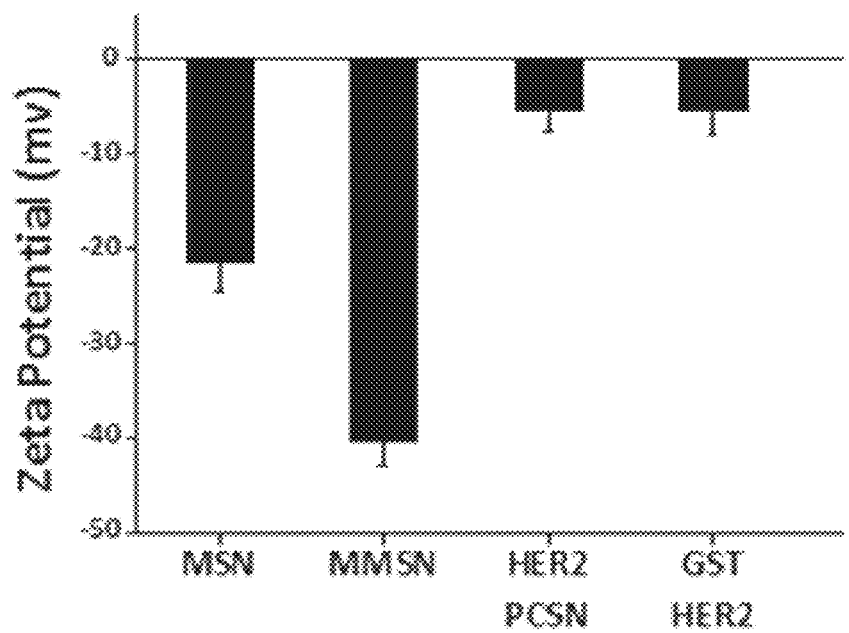

As a result, as shown in FIG. 4A, the surface charge of PCSNs of the present disclosure were found to be similar to that of GST-Afb, as compared with nanoparticles without GST-Afb protein corona as a shield (FIG. 4A). The surface charges of GST-HER2 Afb and GST-Afb EGFR at physiological pH environment were −5.25 mV and −3.5 mV, respectively. In contrast, the surface charge of MSNs was −23 mV, and the surface charge of MMSNs prepared by linking GST to the surface of nanoparticles was −40 mV.

In comparison, with regard to PCSNs surrounded by protein corona shield (PCS), the surface charges of HER2-PCSN and EGFR-PCSN were −5.3 mV and −3.24 mV, respectively, which were similar to that of GST-Afb fusion protein without surface binding of nanoparticles (FIG. 4A).

<3-2> Analysis of Changes in Surface Area and Size of Nanoparticles

Sizes of the nanoparticles prepared in the present disclosure were compared.

Figure 4B:
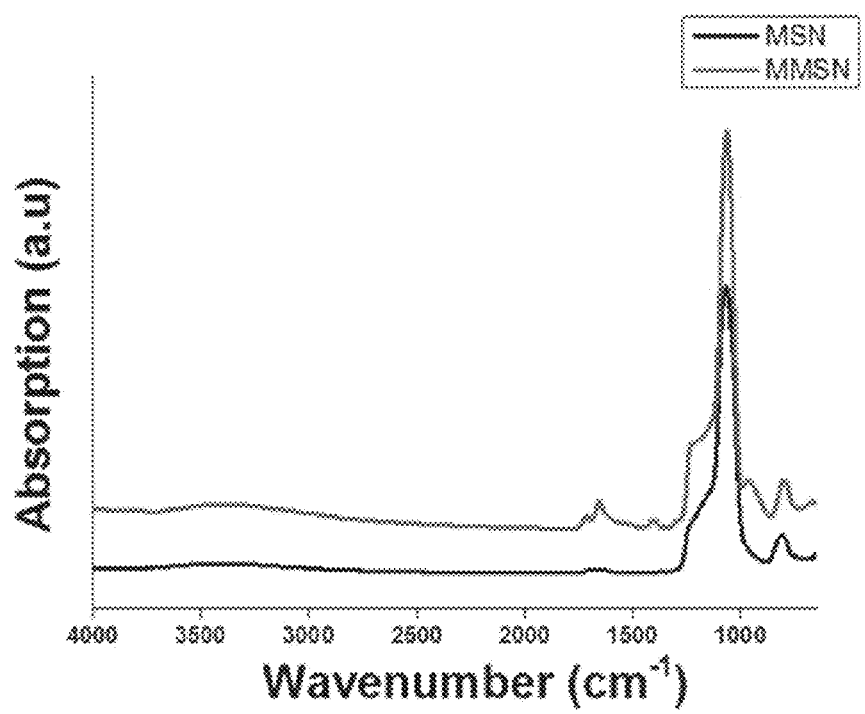

First, to examine reactive groups distributed on the surfaces of MSNs and MMSNs, FTIR analysis was performed. Results of FTIR analysis of MMSNs prepared by attaching GST on the surface of MSNs by chemical bonding showed that, as shown in FIG. 4B, absorption broad bands appeared near 1711 $cm^{-1}$ to 1651 $cm^{-1}$ (symmetric vCOO$^-$), 1409 $cm^{-1}$ (asymmetric vCOO$^-$), and 1711 $cm^{-1}$ (vC=O), indicating that —COOH of GSH was included on the surface of MMSNs (FIG. 4B). Further, no absorption broad band appeared near 2526 $cm^{-1}$, indicating that GSH was bound with acrylate groups on the surface of MSNs via covalent bonds, resulting in no appearance of absorption broad band near the corresponding wavelength (FIG. 4B).

Further, surface areas and pore sizes of MSNs and MMSNs were examined. MSNs having a mean diameter of 103±10 nm were used. As a result, the surface area and pore size as in the following [Table 1] were confirmed, and when MSNs and MMSNs were compared with each other, MMSNs prepared by binding GST onto the surface tend to have smaller surface area and pore volume than MSNs (Table 1).

TABLE 1

Comparison of surface area and pore size between MSN and MMSN

| Sample name | Surface area ($m^2/g$) | Pore volume ($cm^3/g$) | Pore size (nm) |
| --- | --- | --- | --- |
| MSN | 1190 | 1.10 | 2.68 |
| MMSN | 540 | 0.50 | 2.04 |

Figure 4C:
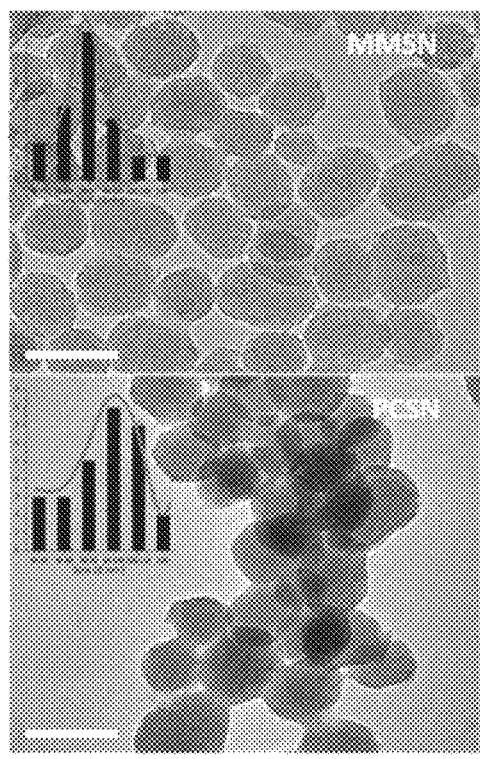

In addition, hydrodynamic radii of MMSNs and PCSNs were measured by performing dynamic light scattering (DLS) to confirm the sizes of nanoparticles. As a result, the radius of MMSNs prepared by binding only GSH without GST-Afb fusion protein was about 140±20 nm, whereas the nanoparticle radii of PCSNs were about 270±20 nm and about 265±31 nm for HER2-PCSN and EGFR-PCSN, respectively, indicating that the radii of PCSNs surrounded by the protein corona shield were increased. TEM image analysis further confirmed that the radii of particles were increased by additional formation of the protein layer on the surface of PCSNs, as compared with MMSNs (FIG. 4C). In the process of preparing PCSN by binding GST-Afb onto the surface of MMSNs, the number of GST-Afb fusion protein forming the protein corona shield on MMSNs was examined by BSA analysis. As a result, it was confirmed that the number of GST-HER2 Afb protein bound onto the surface of HER2-PCSN was 1162±41, and the number of GST-EGFR Afb protein bound onto the surface of EGFR-PCSN was 819±30.

<3-3> Analysis of Storage Stability of PCSNs

To use PCSNs of the present disclosure as a drug delivery carrier, it was examined whether PCSNs may exhibit storage stability to maintain the shape of nanoparticles without aggregation even though stored for a long period of time. To this end, GST-Afb fusion protein and PCSNs having the same as PCS were added to PBS buffer, respectively and stored at 4° C. for 2 weeks, and then aggregation was examined.

Figure 4D:
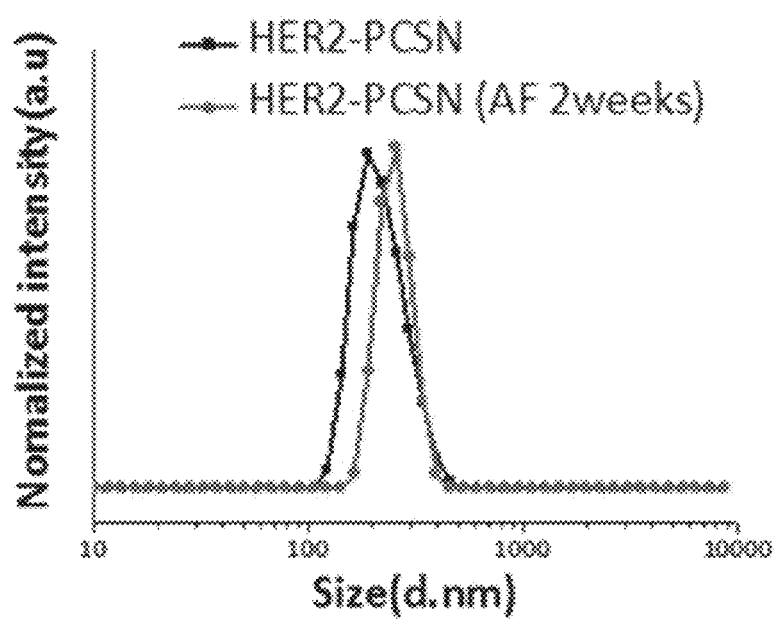

As a result, as shown in FIG. 4D, both GST-Afb fusion protein and PCSNs maintained their structurally intact forms without aggregation even though stored for 2 weeks, and thus their sizes were maintained constant (FIG. 4D).

Example 4. Characterization of Protein Corona Shield Produced on Surface of Nanoparticles <4-1> Examination of Optimal Addition Concentration of GST-Afb in Preparation of PCSNs When formation of the protein corona shield using GST-Afb was first induced in the preparation process of PCSNs, optimal addition concentration of GST-Afb was examined.

Thus, when PCSNs were prepared by the process of Example <2-4>, GST-HER2 Afb or GST-EGFR Afb was mixed at a concentration of 1 μg, 5 μg, 50 μg, 150 μg, or 175 μg per 1 mg of MMSNs to prepare PCSNs. A concentration of the residual protein that remained after inducing a reaction of the mixture of MMSN and GST-Afb was measured to obtain the optimal addition concentration of GST-Afb for forming PCS on the surface of PCSNs.

As a result, the optimal ratio of GST-Afb protein bound onto MMSNs was found to be 50 μg (1008 to 1100 proteins) per 1 mg of MMSNs. It was confirmed that the final amount of the protein forming PCS on the surface of nanoparticles is influenced by the protein concentration during the initial reaction.

<4-2> Examination of Quantity of Protein Forming Protein Corona on Nanoparticle Surface It was examined whether the formation of unwanted protein corona after injection into the living body was suppressed by first forming PCS using GST-Afb on the surface of PCSNs. To this end, MMSNs, PMSNs, and PCSNs were stored in 55% serum for a total of 4 hr, respectively. 1 hr, 2 hr, and 4 hr after initiation of the storage, the respective nanoparticles were collected, and the serum protein layers formed on the surface were separated from the nanoparticles. The separated proteins were loaded on SDS-PAGE to identify protein bands. Intensities of the identified protein bands were subjected to quantitative analysis.

Figure 5A:
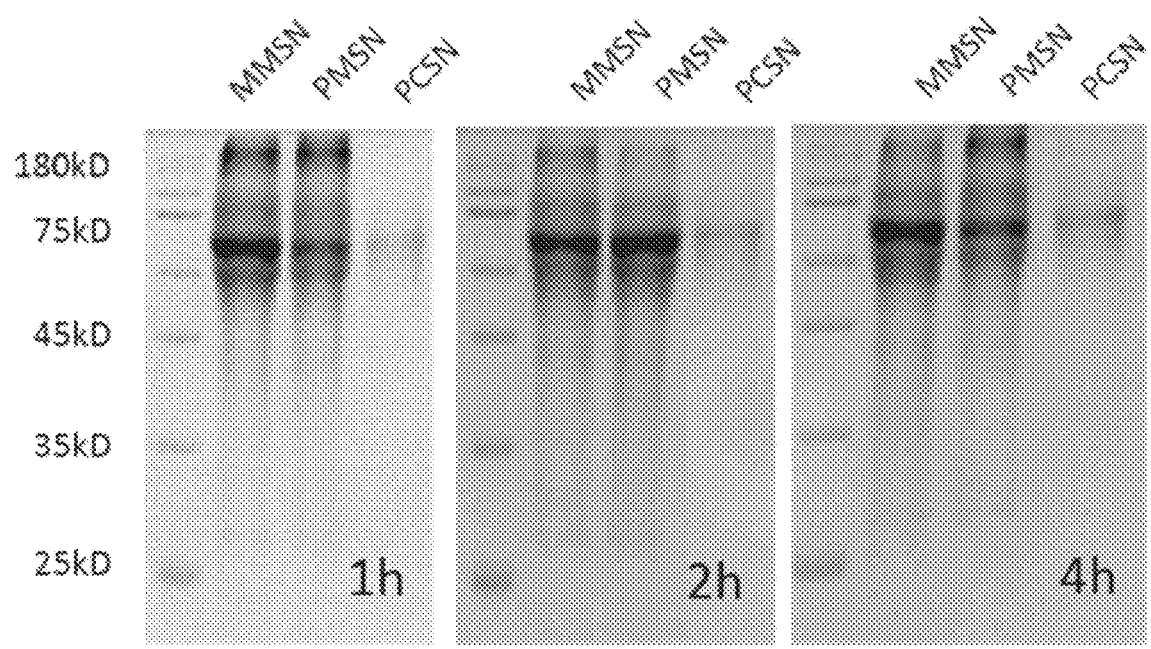
Figure 5B:
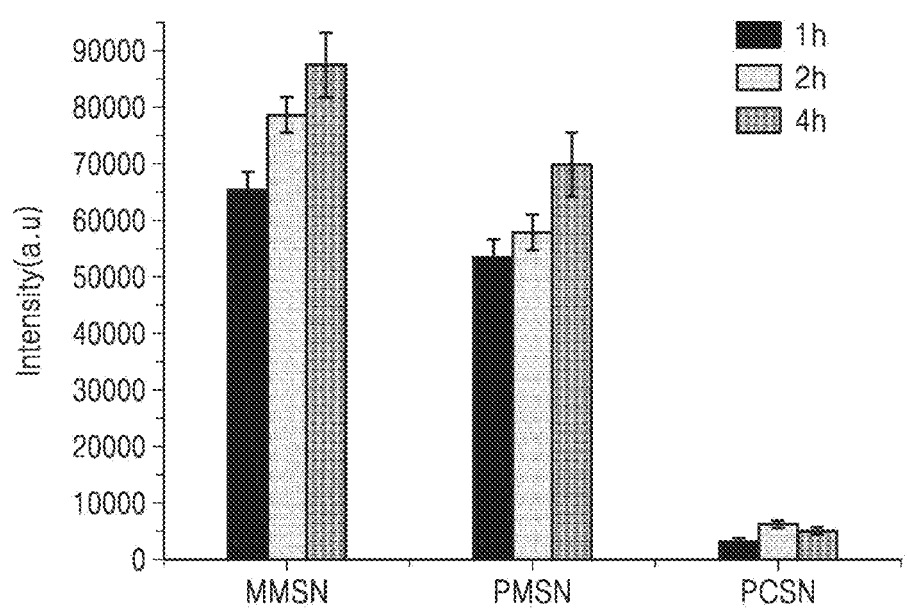

As a result, as shown in FIG. 5, the level of serum proteins bound on the surface of PCSNs was remarkably reduced, as compared with the serum proteins bound on the surface of MMSNs or PMSNs (FIGS. 5A and 5B). In particular, the levels of serum proteins bound onto the surface of MMSNs and PMSNs were increased with increasing time of storage in serum, whereas a small amount of serum proteins was bound onto the surface of PCSNs regardless of the passage of time.

<4-3> Proteomic Study of Serum Proteins Bound Onto Surface of Nanoparticles

It was confirmed that the remarkably reduced level of proteins layer was bound onto the surface of PCSNs, unlike MMSNs and PMSNs. Therefore, to examine kinds of the proteins attached onto the respective nanoparticles, analysis was performed in a proteome level.

In detail, the protein bands identified by loading on SDS-PAGE in Example <4-2> and Coomassie blue staining were sliced into six consecutive portions by in-gel tryptic digestion. The resulting tryptic peptides were analyzed by LC-MS/MS, and the molecular weights of the corresponding peptides were analyzed on an Orbitrap ELITE (Thermo, Bremen, Germany) equipped with a nanoelectrospray ion source. As conditions for HPLC analysis performed for separating the peptide mixture in LC-MS/MS, a C18 reverse-phase column (500 mm×75 µg ID) was used as an HPLC column. Analysis was performed for a total of 150 min with a concentration gradient of a mixture of acetonitrile and 0.1% formic acid as a mobile phase solvent, and a flow rate of the mobile phase was maintained at 300 nL per min. Conditions of MS/MS analysis for analyzing the molecular weights of the separated peptides are as follows: MS spectrum (m/z 350~1600) of precursor ion scan were performed in Orbitrap with a resolution of 60,000 at m/z 400 with an internal lock mass. Among them, the 20 most intensive ions were fragmented in a linear ion trap by collisionally induced dissociation (CID). LC-MS/MS results were analyzed using Sequest (Thermo Fisher Scientific, San Jose, CA, USA; Version 1.4.1.14) and X! Tandem (The GPM, thegpm.org; version CYCLONE (2010.12.01.1)) program. Sequences of the proteins analyzed by using the two programs were analyzed, based on Bos taurus protein sequence database (8244 entries, UniProt (http://www.uniprot.org/)), thereby identifying the corresponding proteins. The identified proteins were classified, based on Protein Prophet algorithm (Mueller, L. N., Brusniak, M.-Y., Mani, D. & Aebersold, R. *Journal of proteome research* 7, 51-61 (2008)), and functions of the proteins were analyzed using GO terms available from NCBI.

Figure 6A:
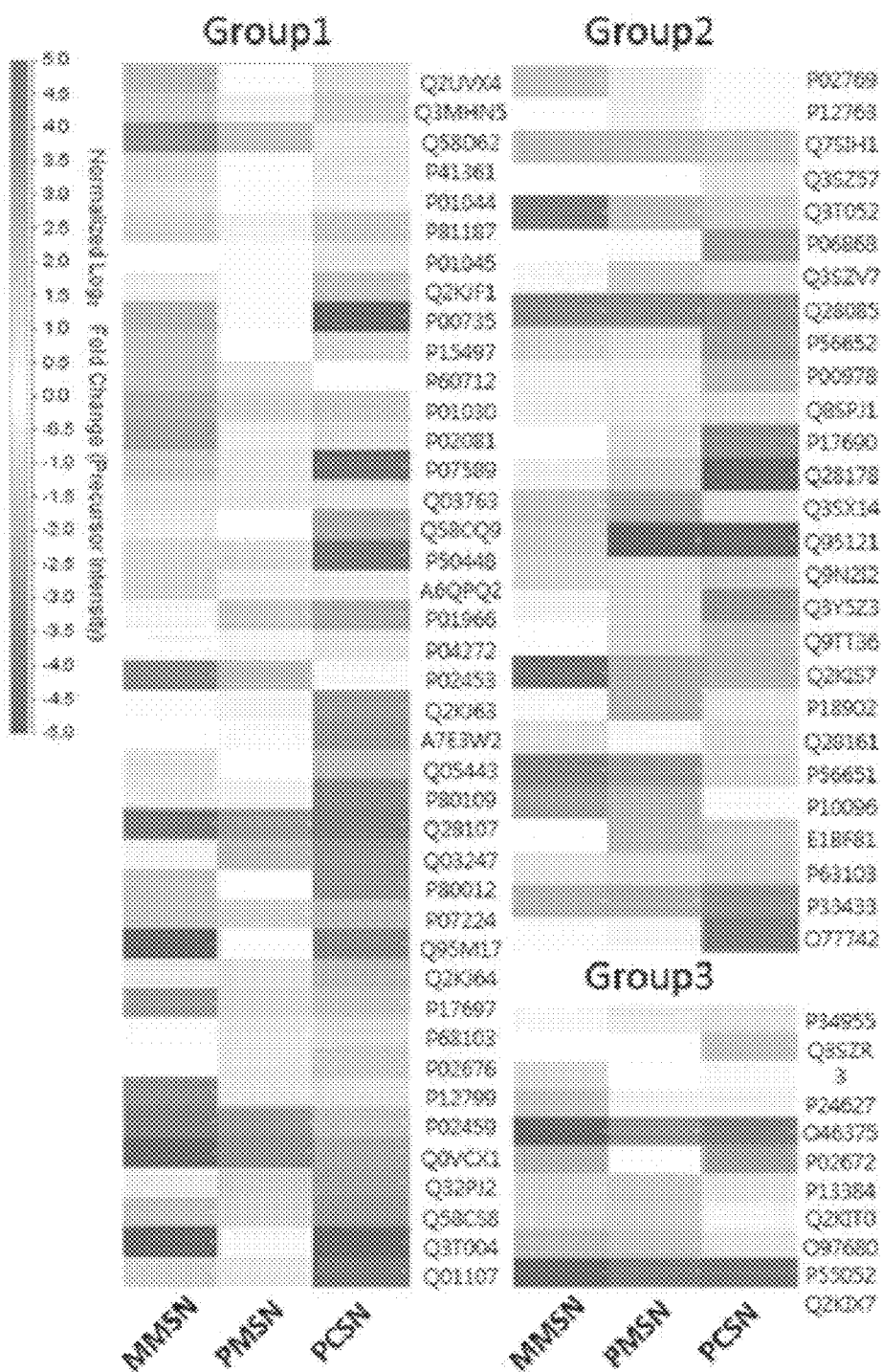

As a result, as shown in FIG. 6, proteins attached to the surfaces of PMSNs, MMSNs, and PCSNs were a total of 183 proteins, and among them, the 78 most abundant proteins were shown in a heat map (FIG. 6A). The respective proteins were divided into a total of three groups, based on the binding patterns on PMSNs, MMSNs, and PCSNs. The most kinds of serum proteins belonged to Group 1, and proteins of Group 1 were classified according to the decreasing amount of the proteins bound to MMSNs, PMSNs, and PCSNs in this order. Further, proteins of Group 2 were classified according to proteins bound to MMSNs and PMSNs in similar levels, and proteins of Group 3 were classified according to proteins bound to nanoparticles of MMSNs, PMSNs, and PCSNs all in similar levels (FIG. 6A). As a result, it was confirmed that PCS of surrounding the surface of PCSNs with GST-Afb protein functions to protect nanoparticles and blocks binding with serum proteins, as compared with MMSNs and PMSNs, leading to the reduced amount of serum proteins bound to PCSNs.

Figure 6B:
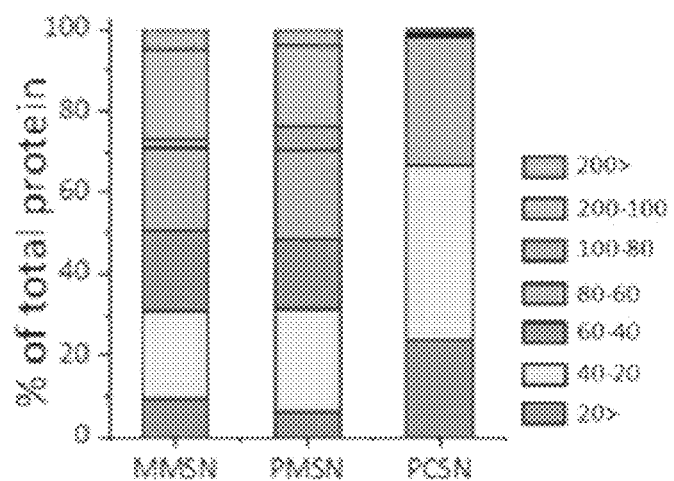
Figure 6C:
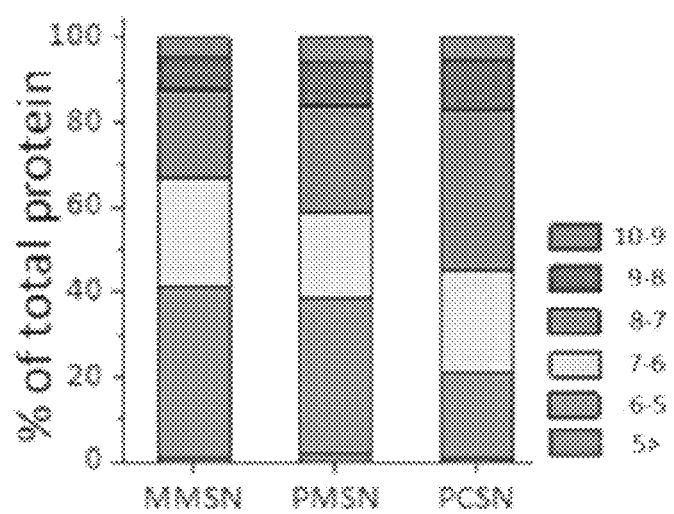

Next, the bound proteins were classified according to their molecular weight and isoelectric point. As a result, MMSNs and PMSNs showed that serum proteins were bound to the surface thereof in the similar patterns according to the molecular weight of the protein, whereas PCSNs showed different protein binding patterns. Specifically, on the surface of PCSNs, a ratio of the proteins having a low molecular weight of 20 kDa to 80 kDa was higher than the proteins having a molecular weight of 100 kDa or more (FIG. 6B). With regard to the isoelectric point, a high binding ratio of the proteins with PI of about 7 to about 8 was observed on the surface of PCSNs (FIG. 6C).

Figure 6D:
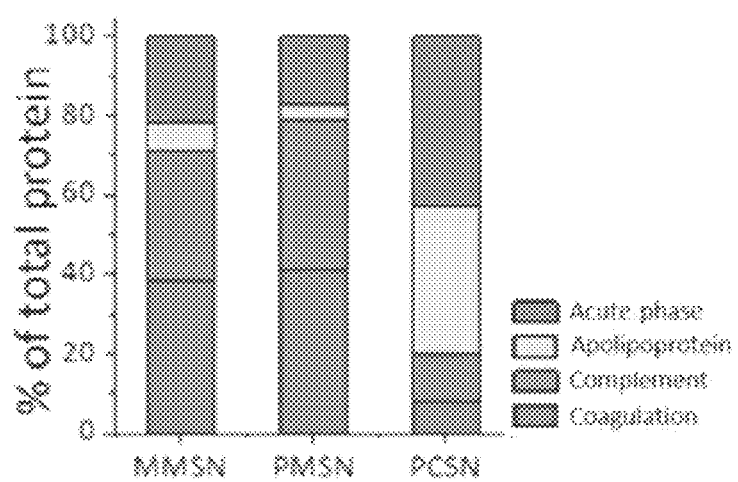
Figure 6E:
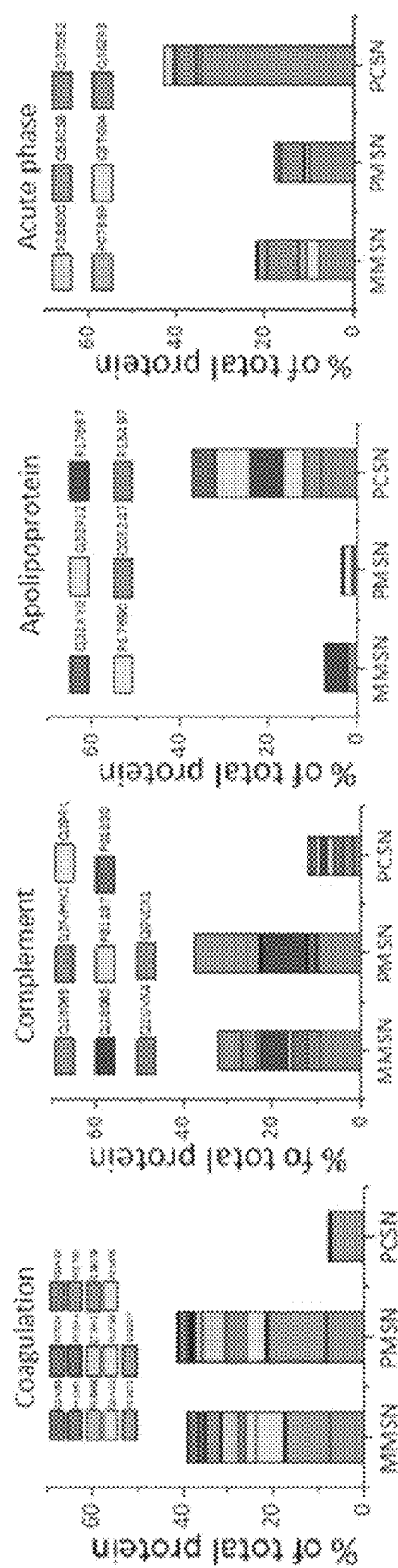

Further, the bound proteins were classified according to their functions. When the serum proteins were classified according to their functions, proteins involved in immune responses such as coagulation or complement were mainly bound, and divided into a total of four groups (FIG. 6D). When these proteins were compared with regard to MMSNs, PMSNs, and PCSNs, MMSNs and PMSNs exhibited similar protein binding patterns, in which serum proteins involved in coagulation and complement proteins were bound at a high ratio, whereas serum proteins involved in the acute phase and apolipoproteins were bound at a higher ratio on the surface of PCSNs (FIGS. 6D and 6E).

These results confirmed that, in PCSNs of the present disclosure, the kind of the serum proteins may be controlled and the number of proteins may be blocked through first formation of the corona shield surrounding the surface of nanoparticles by using GST-Afb protein, thereby inhibiting formation of protein corona surrounded by the serum proteins. Due to this function, when PCSNs of the present disclosure are injected into in vivo environment, PCSNs may migrate to tumor tissues to exhibit improved targeting ability without phagocytic clearance of macrophages.

Example 5. Examination of Tumor Cell Targeting Ability and Drug Delivery Capability of Nanoparticles with GST-Afb Shield <5-1> Examination of Tumor Cell Targeting Ability of PCSNs It was confirmed that since PCSNs are prepared by forming the corona shield using GST-Afb protein on the surface of nanoparticles, binding of serum proteins thereto were blocked. Thus, it was examined whether PSCNs maintain and exhibit characteristics as a drug delivery carrier even though GST-Afb protein is bound to the surface thereof.

Specifically, HeK-293T cell which is a human embryonic kidney cell line used for a normal control, SK-BR-3 cell which is a breast cancer cell line expressing a receptor recognized by HER2 Afb, and MDA-MB-468 cell which is a breast cancer cell line expressing a receptor recognized by EGFR Afb were seeded in two-well chambers with a cover glass at a density of 2×10$^5$ cells/well, respectively. After seeding, the cells were incubated for 24 hr, and treated with camptothecin (CPT)-loaded nanoparticles at a final CPT concentration of 10 µg/mL, respectively. SK-BR-3 cells and HeK-293T cells were treated with HER2-PCSN, respectively and MDA-MB-468 cells and HeK-293T cells were treated with EGFR-PCSN, respectively. With regard to treatment with CPT-loaded PCSNs, localization of MSN in cells treated with nanoparticles of FITC-conjugated MSN was examined by observing fluorescence at green wavelength. To stain cells, Lysotracker red (FM DND-99, Invitrogen) which is a kit staining lysosomes in live cells was used. After respective cells were treated with PCSNs, cells and MSN localization were observed under a fluorescence microscope over time.

To examine cellular uptake of the drug, Dil-loaded nanoparticles were used. HeK293T cells, SK-BR-3 cells, and MDA-MB-468 cells were seeded into 6-well plates at a density of $1\times10^6$ cells/well and incubated at 37° C. for 24 hr. Thereafter, the cells were treated with Dil-loaded nanoparticles and incubated, respectively. At this time, the cells were treated with Dil at a final concentration of 0.20 µg/ml. After incubation, the respective cells were treated with tripsin to collect cells, which were then washed with PBS, suspended, and injected into a flow cytometer equipped with BD-FACS Caliber to examine color development of intracellular Dil dye. At this time, lysosomes in the cells were stained using Lysotracker green (FM DND-26, Invitrogen). To examine fluorescence development of Dil dye, at least 10,000 cells were injected into a flow cytometer, followed by analysis. The obtained results were analyzed using a FlowJo software.

Figure 7A:
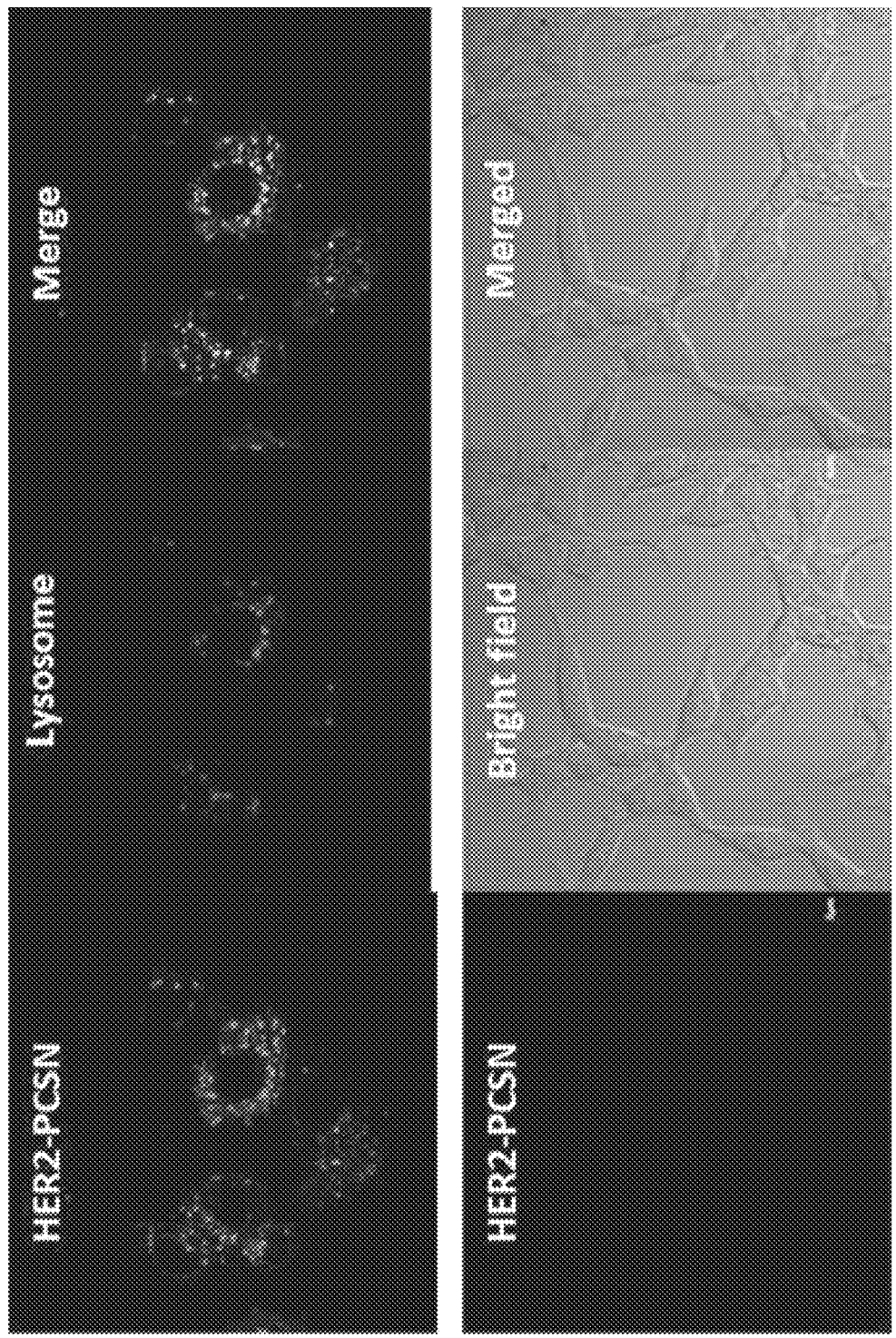
Figure 7C:
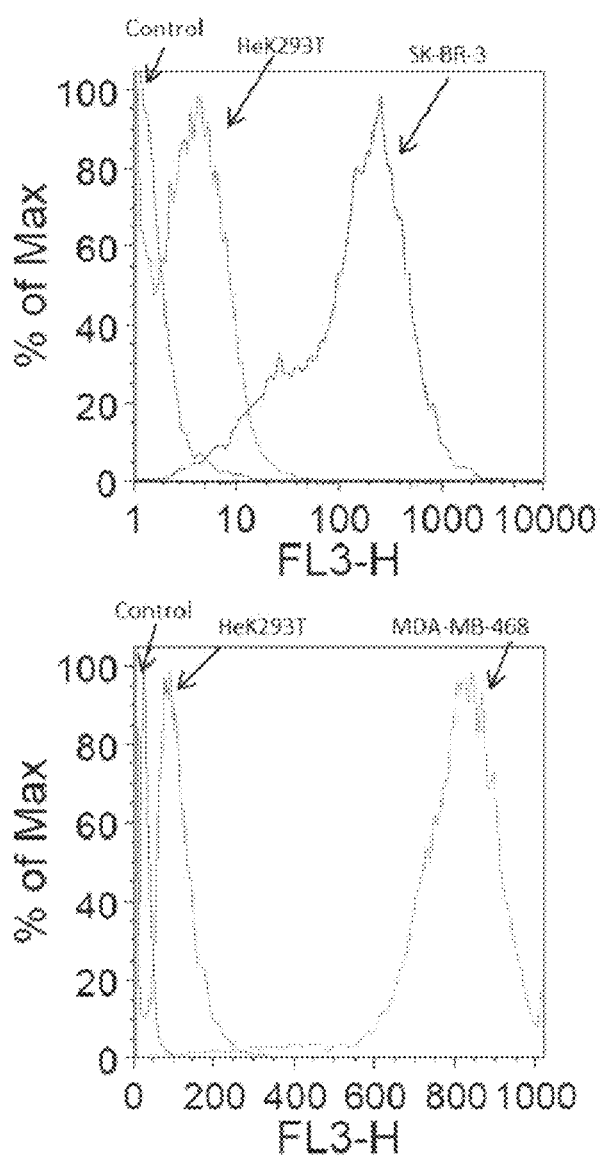

As a result, as shown in FIG. 7, the respective cell lines were treated with CPT or Dil-loaded PCSNs to examine their localization. First, it was confirmed that when target cancer cells were treated with CPT-loaded PCSNs, HER2-PCSNs may significantly recognize the surface of SK-BR3 cells which are tumor cells targeted by HER2 Afb (FIG. 7A), and EGFR-PCSNs may significantly recognize the surface of MDA-MB 468 cells which are tumor cells targeted by EGFR Afb (FIG. 7D). When these results are compared with the result of HeK-293T cell which is a normal cell line, both HER2-PCSNs and EGFR-PCSNs did not bind to the surface of HeK-293T cells, indicating that the PCSNs of the present disclosure may exhibit specific targeting ability with respect to target cancer cells. In particular, to examine localization of PCSNs in cells treated therewith, when FITC was conjugated to a functional group of GSH and analyzed under a fluorescence microscope, uptake of nanoparticles into cancer cells was not observed, but nanoparticles remained on the surface of cells (FIG. 7E).

<5-2> Evaluation of Drug Release from PCSNs into Tumor Cells

It was confirmed that PCSNs may exhibit specific targeting ability with respect to tumor cells targeted by affibody bound on the surface of PCSNs, and thus it was examined whether PCSNs may significantly release the drug loaded therein after targeting cancer cells.

In detail, before preparing EGFR-PCSNs, FITC was covalently linked to the GSH group of GST-EGFR Afb, and then prepared as PCSNs, and camptothecin (CPT) was loaded therein to prepare nanoparticles. Thereafter, MDA-MB-468 cells or HeK-293T cells were incubated, respectively and treated with the prepared nanoparticles at a final CPT concentration of 10 µg/ml, respectively. Then, the cells were further incubated for 16 hr, and CPT and FITC locations were observed under a fluorescence microscope over time.

Figure 8:
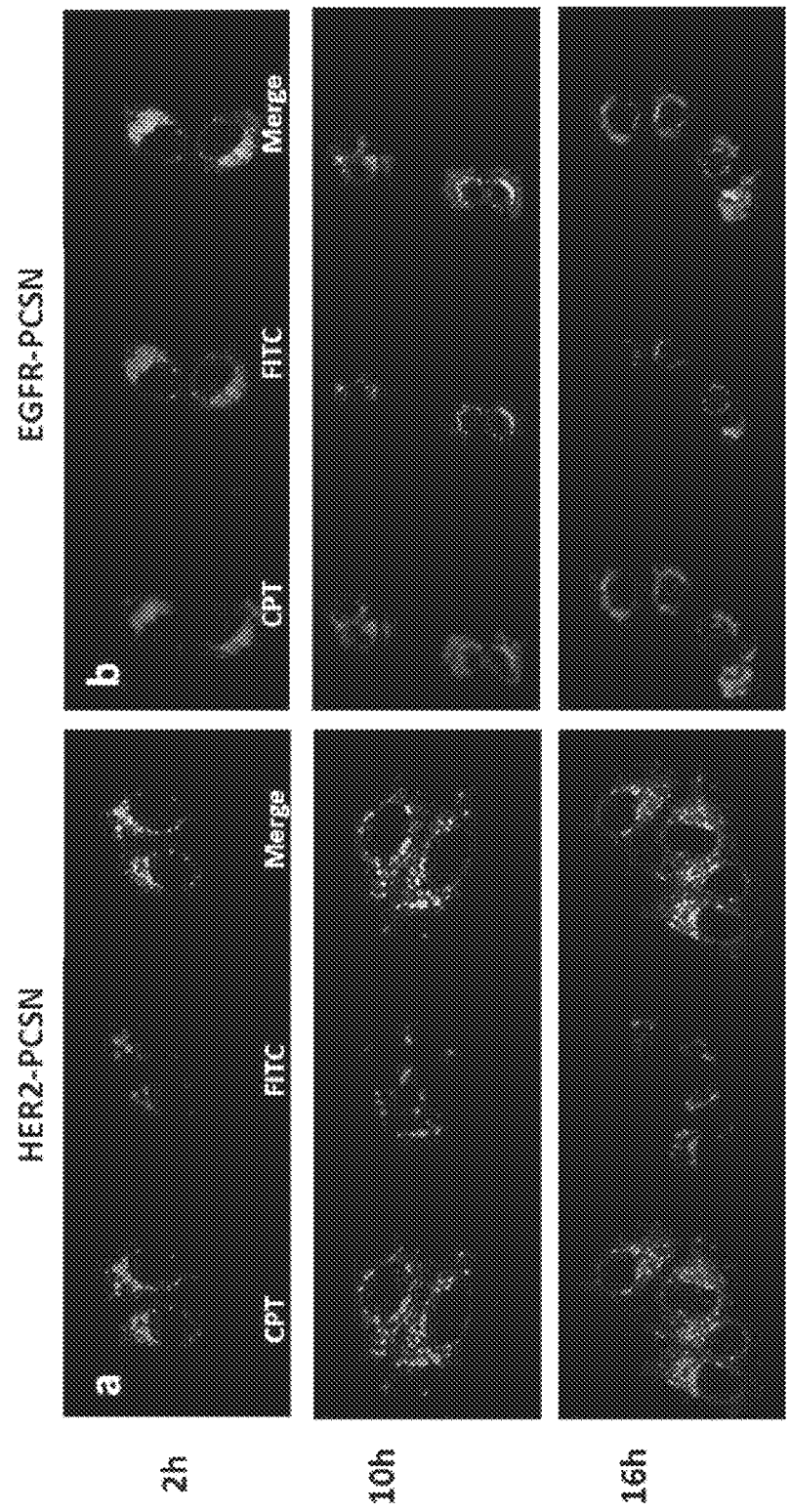

As a result, as shown in FIG. 8, in the early stage of addition of the drug-loaded PCSNs, PCSNs were located around the target cells, and at the same time, the drug (CPT) was also located around the cells, and for this reason, the fluorescence signals were overlapped. As time passed, entry of drug into the cells was observed, and degradation of FITC signals of PCSNs was observed around the cells (FIGS. 8A and 8B). These results indicate that when drug-loaded PCSNs are administered into in vivo environment, the drug loaded inside PCSNs may be released to enter cells, and PCSNs are degraded, resulting in significant treatment of cancer cells with the drug.

<5-3> Examination of Cytotoxicity of PCSNs Against Target Cells

Since PCSNs exhibit significant targeting ability with respect to target cells and release of drugs into cells, it was examined whether cancer cells were killed thereby.

In detail, CPT-loaded HER2-PCSNs and EGFR-PCSNs were prepared, respectively and treated to HeK293T cells, SK-BR-3 cells, or MDA-MB-468 cells at a CPT concentration of 0.01 µg/ml, 0.1 µg/ml, 0.25 µg/ml, 0.5 µg/ml, 1.0 µg/ml, 2.5 µg/ml, and 5.0 µg/ml, respectively, followed by incubation. After completing incubation, cell viability was examined using an alamar blue dye (DAL 2015, Invitrogen, Korea).

Figure 9A:
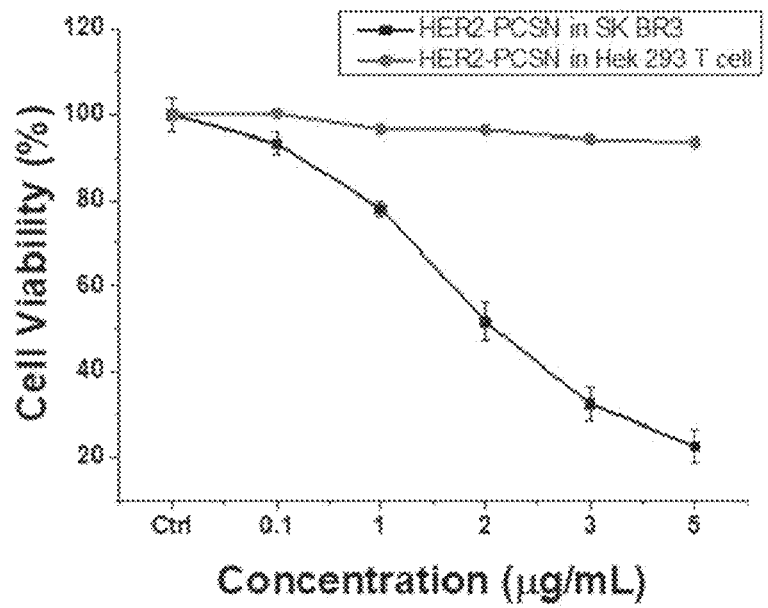
Figure 9B:
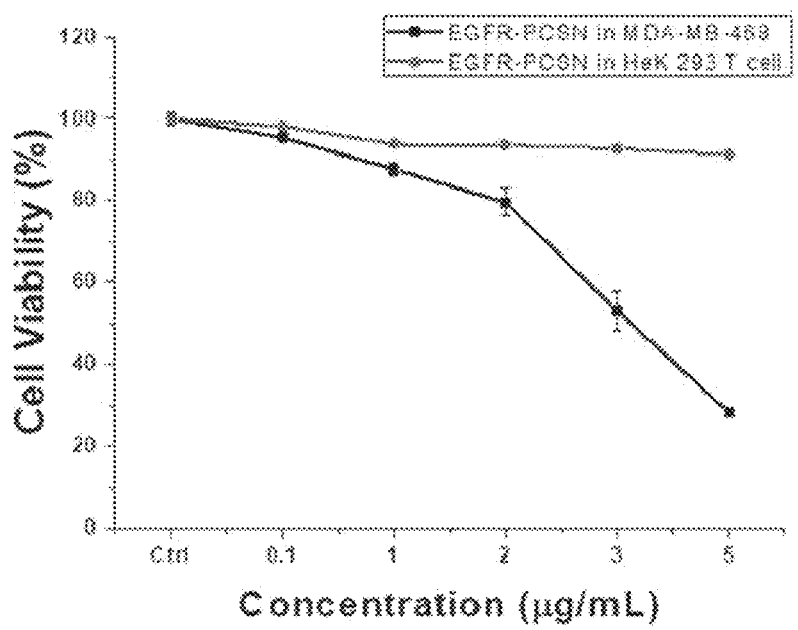
Figure 10A:
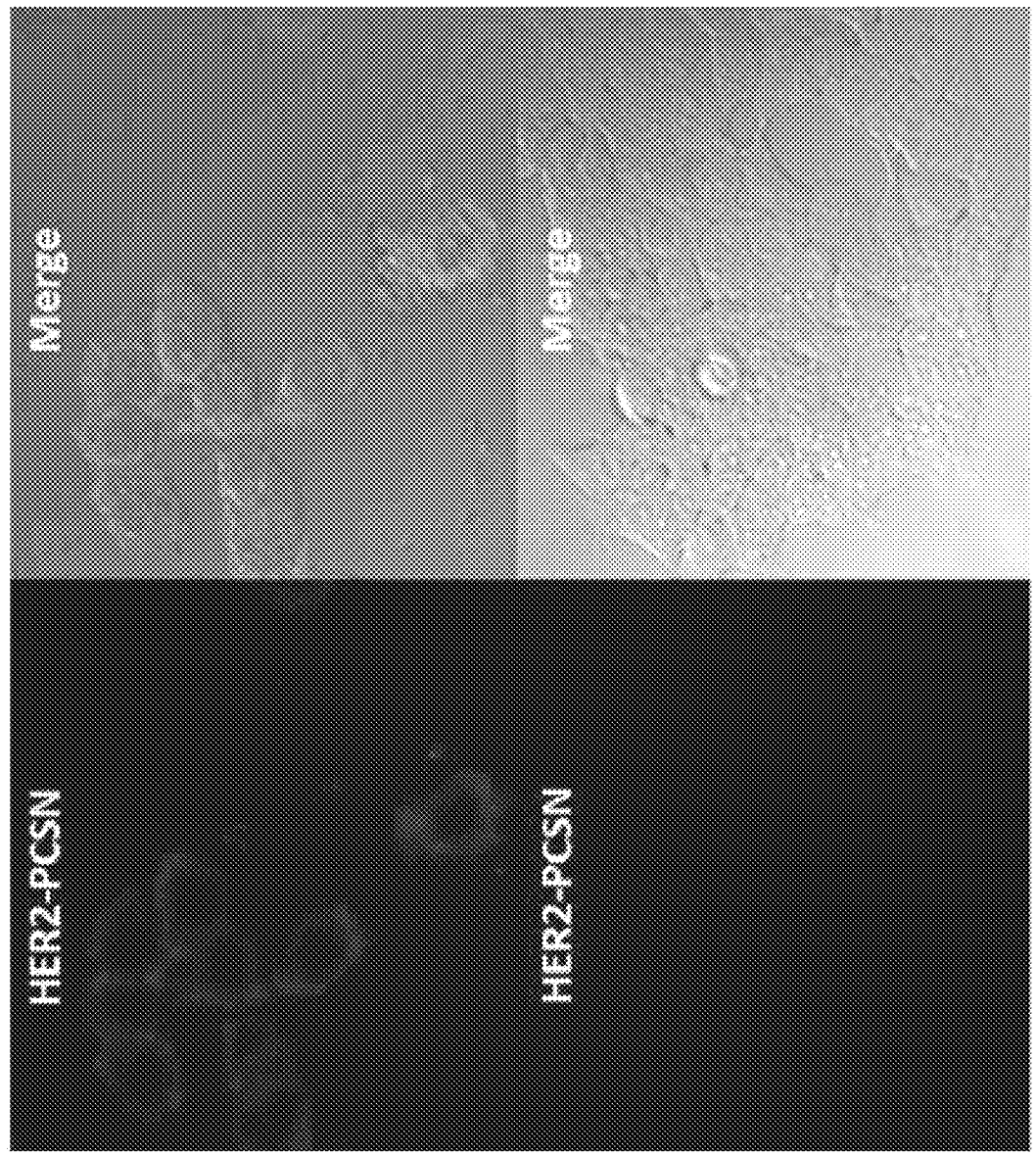
Figure 10B:
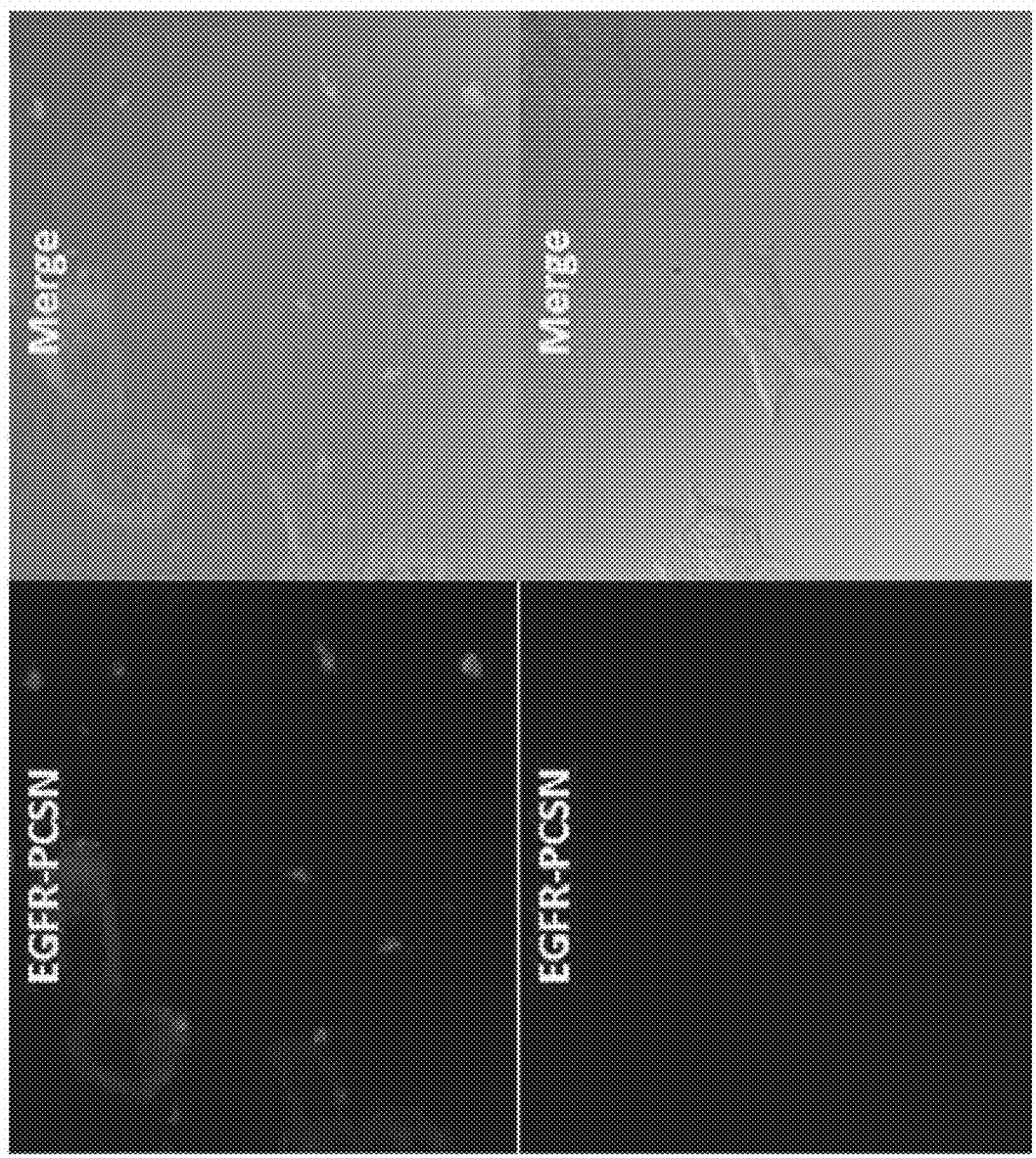
Figure 10C:
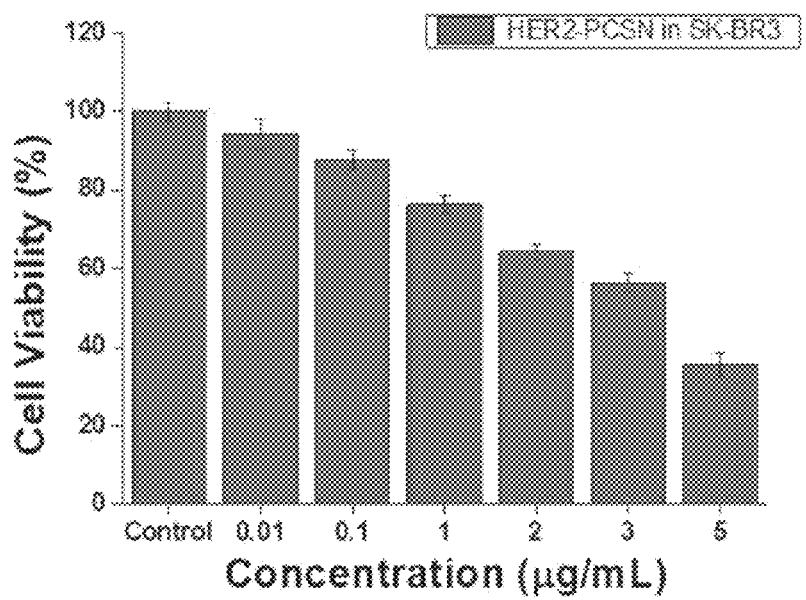
Figure 10D:
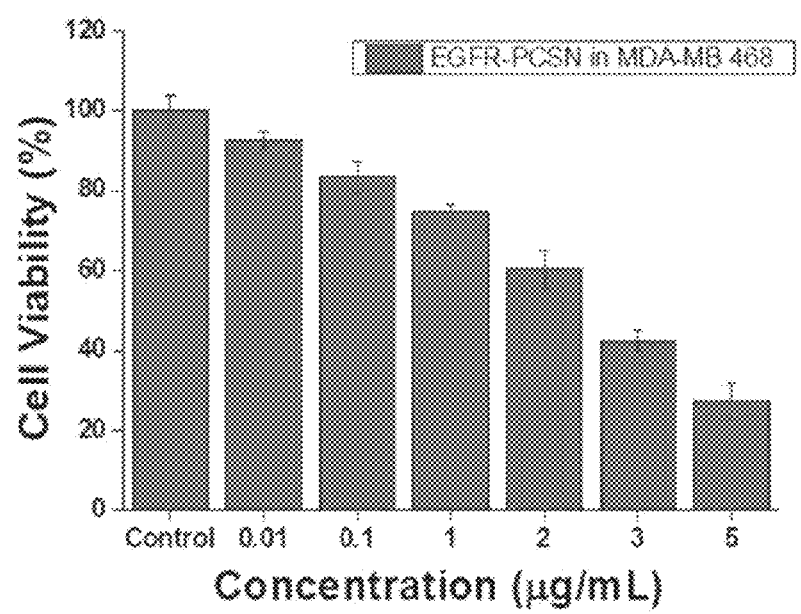

As a result, as shown in FIG. 9, it was confirmed that both HER2-PCSNs and EGFR-PCSNs may significantly induce release of the drug into the target tumor cells, respectively, and accordingly, tumor cell-killing effect was also increased with increasing treatment concentration of PCSNs (FIGS. 9A and 9B). In contrast, it was confirmed that death of the normal cell HeK293T was not observed even though the treatment concentration of PCSNs was increased, indicating that PCSNs of the present disclosure exhibit no cytotoxicity against normal cells, thereby being used as a safe drug delivery carrier.

<5-4> Examination of Changes of Targeting Ability and Cytotoxicity of PCSNs According to Loaded Drugs It was confirmed that when PCSNs of the present disclosure are prepared, the dye Dil or drug CPT-loaded PCSNs may exhibit significant cell targeting ability and cytotoxicity. Thus, the CPT drug was replaced by doxorubicin (DOX) to prepare drug-loaded PCSNs. Thereafter, it was examined whether HER2-PCSNs and EGFR-PCSNs exhibit the drug delivery effect and cell killing effect against target cells, respectively.

As a result, as shown in FIG. 10, it was confirmed that doxorubicin-loaded PCSNs also exhibited target cell-specific targeting ability, and thus the cell killing effect was increased with increasing PCSN treatment concentrations (FIGS. 10A to 10D). These results suggest that, since a specific chemical reaction with the drug is not required inside the nanoparticles, it is possible to replace the drug with a wanted drug or dye, and the significant drug delivery effect may be achieved due to the surface structure of PCSNs.

Figure 11A:
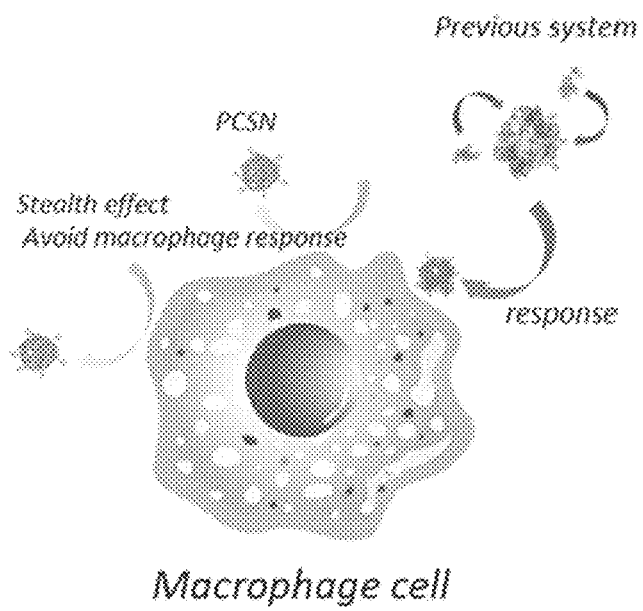

Example 6. Examination of Stealth Effect of Nanoparticles With GST-Afb Shield Against Macrophages To allow delivery of nanocarriers to target tumor tissues in an actual biological environment, it is necessary for the nanoparticles to remain in the blood circulation for a long time. However, due to the attachment of other proteins onto the surface of the nanoparticles to which functional groups are bound, there is a limitation that nanoparticles may be removed by macrophages which is one of the immune systems, and may not exhibit a significant drug delivery effect. To achieve a significant drug delivery effect using nanoparticles as the drug delivery carrier, it is required to avoid and overcome immune responses by these autophagic cells, which is called a stealth effect (FIG. 11A).

<6-1> Examination of PCSN Phagocytosis of Macrophages

Figure 11B:
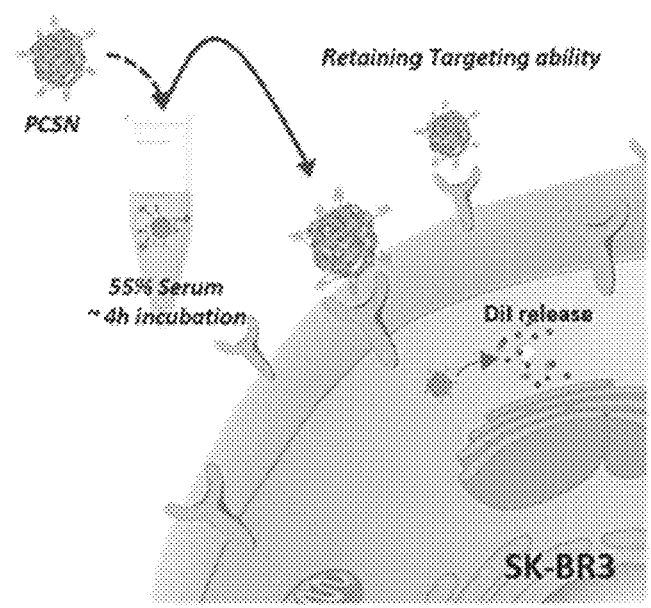

The present inventors tried to confirm whether PCSNs of the present disclosure may exhibit a stealth effect by avoiding phagocytosis by macrophages (FIG. 11B). PEGylated nanoparticles (PMSNs) are used as drug delivery carriers in the prior art, but they are known to have a limitation in the drug delivery effect due to phagocytosis of macrophages. Thus, PMSNs were used as a control nanoparticle for PCSNs.

In detail, DiI-loaded PMSNs or HER2-PCSNs were added to 55% fetal bovine serum (FBS) and allowed to react at 37° C. for 1 hr, and then unbound proteins on the surface of nanoparticles were removed by centrifugation and then washed with PBS to prepare nanoparticles. Next, RAW 264.7 cells which are macrophages were seeded at a density of $1\times10^6$ cells/well in a 6-well plate, and then incubated at 37° C. for 24 hr. After incubation, the cells were treated with the prepared nanoparticles, and further incubated for 6 hr. The incubated cells were treated with DAPI to stain the nuclei, and then fluorescence development of DAPI and DiI was observed under a fluorescence microscope. Further, RAW 264.7 cells were treated with tripsin to collect cells, and then injected into a flow cytometer to examine color development of intracellular DiI dye.

As a result, as shown in FIG. 12, it was confirmed that DiI dye (free DiI) not loaded in nanoparticles was internalized into cells by phagocytosis of macrophages. It was also confirmed that when PMSNs were treated, fluorescence development of DiI internalized into cells was also observed. In contrast, in the case of PCSNs, DiI was not internalized into cells, and thus color development of DiI was not observed (FIGS. 12A to 12D). Therefore, it was confirmed that the GST fusion protein on the surface of PCSNs of the present disclosure may effectively block external proteins, and therefore, PCSNs may remain without clearance because of exhibiting the stealth effect against immune cells even in vivo environment.

<6-2> Examination of Cytotoxicity of PCSNs Against Macrophage

It was confirmed that PCSNs of the present disclosure are not removed by immune responses by macrophages, and thus whether CPT-loaded PCSNs exhibit cell killing effects on macrophages was examined.

In detail, CPT-loaded HER2-PCSNs were prepared and stored in a high concentration of serum protein environment of 55% FBS for 1 hr. Thereafter, the stored HER2-PCSNs were collected and washed, and then treated to RAW 264.7 cells at a CPT concentration of 0.01 µg/ml, 0.1 µg/ml, 0.25 µg/ml, 0.5 µg/ml, 1.0 µg/ml, or 2.5 µg/ml, followed by incubation for 48 hr. After completing incubation, cell viability was examined using an alamar blue dye. As a control for comparison of the cell killing effect, RAW 264.7 cells were treated with free CPT which was not loaded in nanoparticles, and cell viability thereof was examined.

Figure 12A:
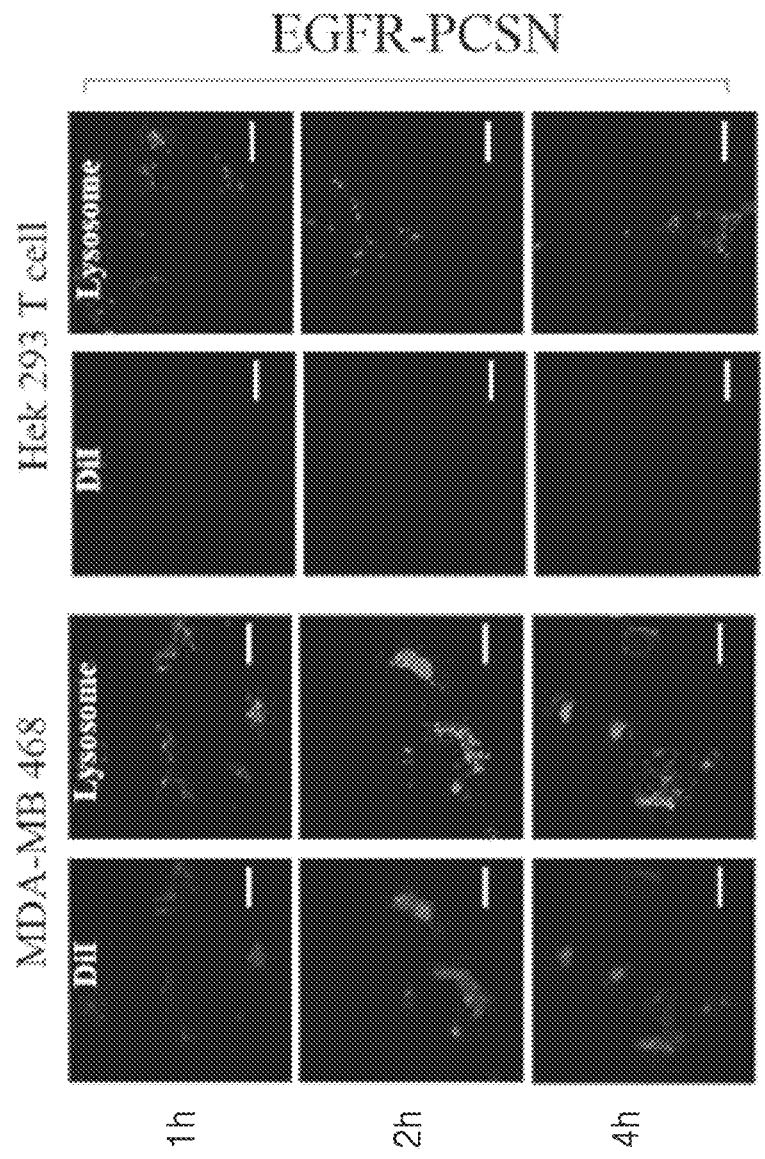
Figure 12C:
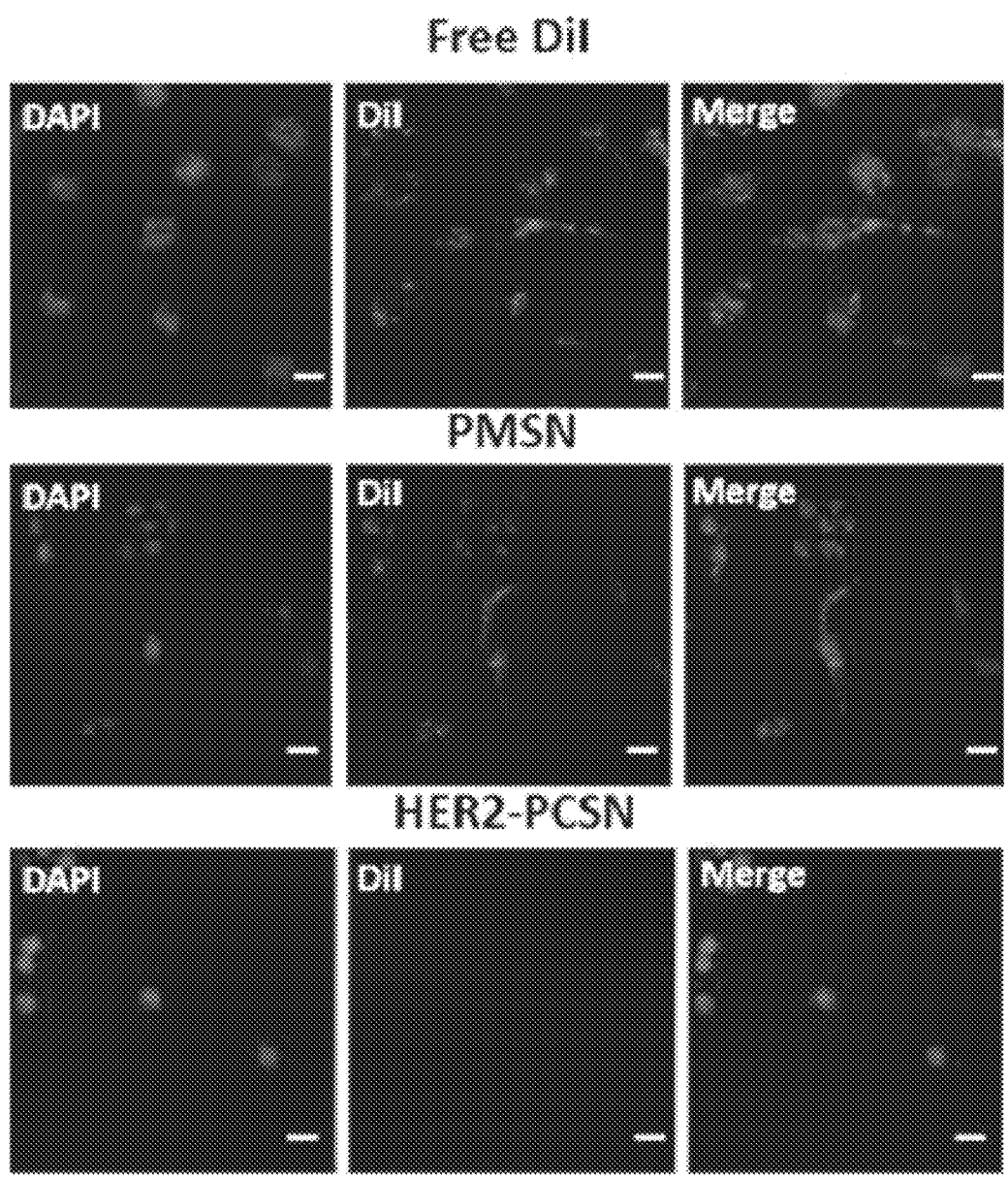
Figure 12D:
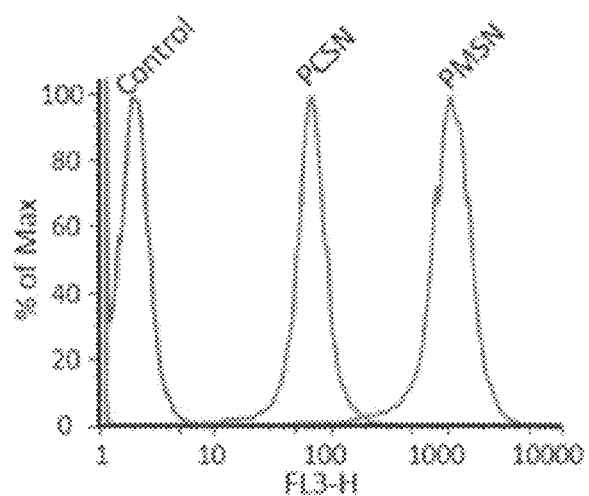
Figure 12E:
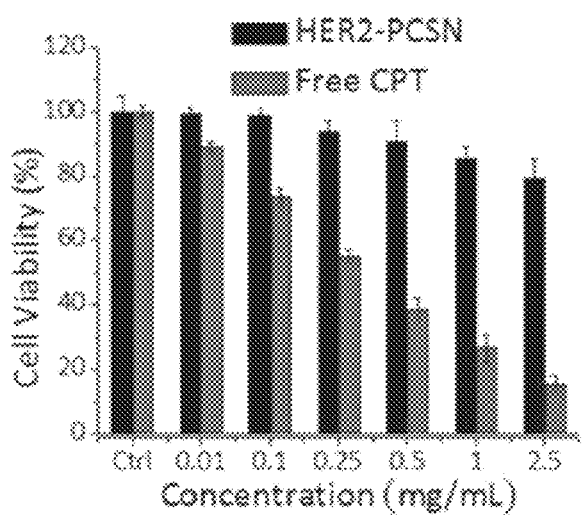

As a result, as shown in FIG. 12E, free CPT which was not loaded in PCSNs exhibited the cell killing effect on RAW 264.7 cells with increasing treatment concentrations, whereas CPT loaded in HER2-PCSNs exhibited no killing effect on macrophages because of not being released from macrophages (FIG. 12E).

<6-3> Examination of Tumor Cell Targeting Ability of PCSNs Stored In Vivo Environment Since PCSNs of the present disclosure exhibit stealth effect without clearance by macrophages even after stored in a high concentration of serum environment, it was examined whether PCSNs may also exhibit significant targeting ability and cell killing effect against cancer cells in vivo environment.

In detail, DiI-loaded HER2-PCSNs were prepared and stored in a high concentration of serum protein environment of 55% FBS for 1 hr. Thereafter, the stored HER2-PCSNs were collected and washed, and then treated to Hek293T cells or SK-BR3 cells, followed by further incubation for 4 hr. After completing incubation, intracellular lysosomes were stained using Lysotracker green (FM DND-26, Invitrogen), and localizations of DiI and lysosomes were examined under a fluorescence microspore. SK-BR3 cells were also treated with CPT-loaded HER2-PCSNs in the same manner as above, and incubated, and then lysosomes were stained using Lysotracker green (FM DND-26, Invitrogen), and localizations of CPT and lysosomes were examined under a fluorescence microspore.

To examine cell killing effects, Hek293T cells or SK-BR3 cells were treated with CPT-loaded HER2-PCSNs at a CPT concentration of 0.1 µg/ml, 1.0 µg/ml, 2.0 µg/ml, 3.0 µg/ml, or 5.0 µg/ml, respectively, followed by incubation for 48 hr. After completing incubation, cell viability was examined using an alamar blue dye.

Figure 13A:
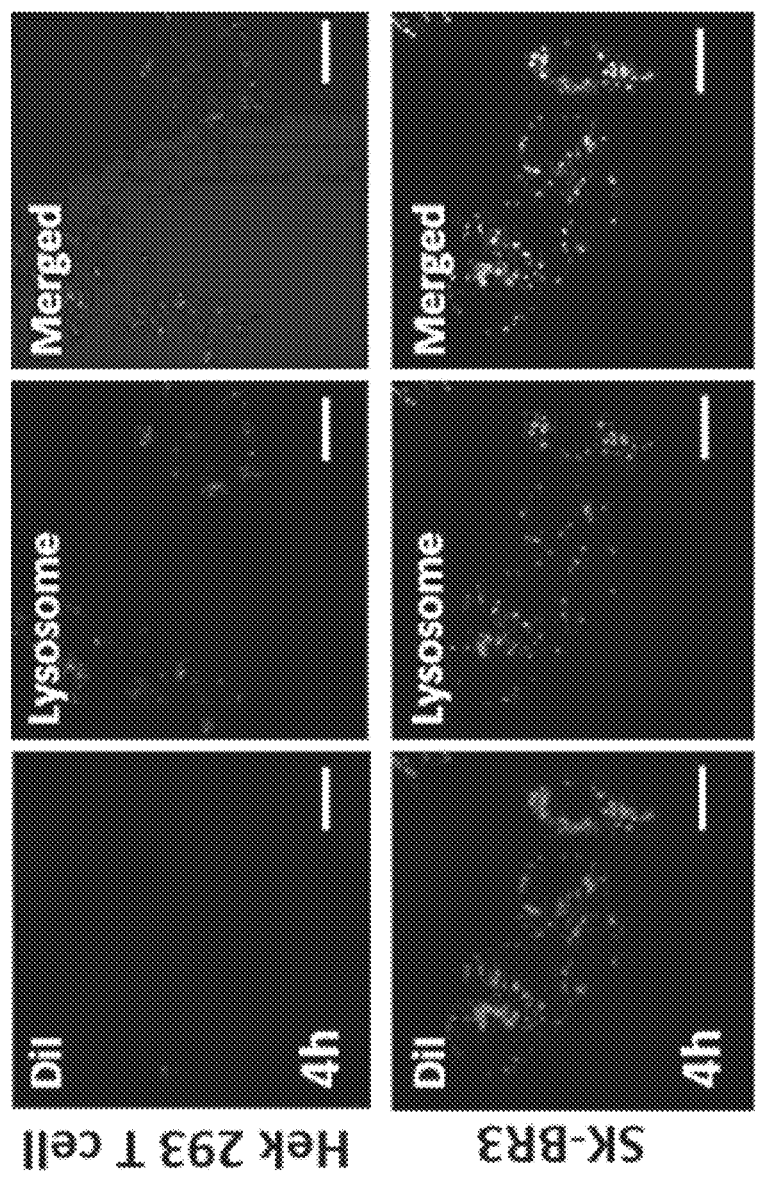
Figure 13B:
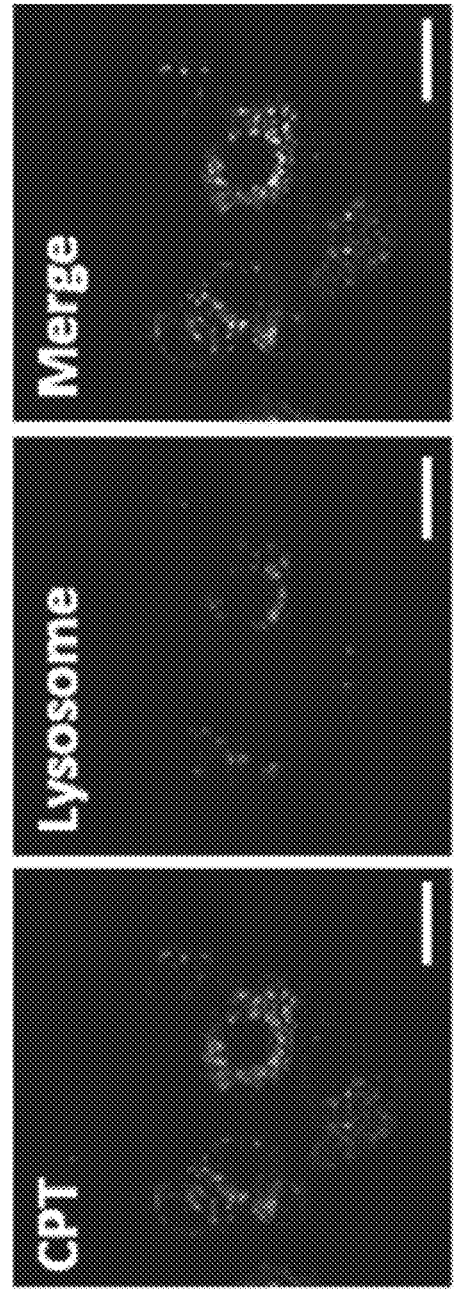
Figure 13C:
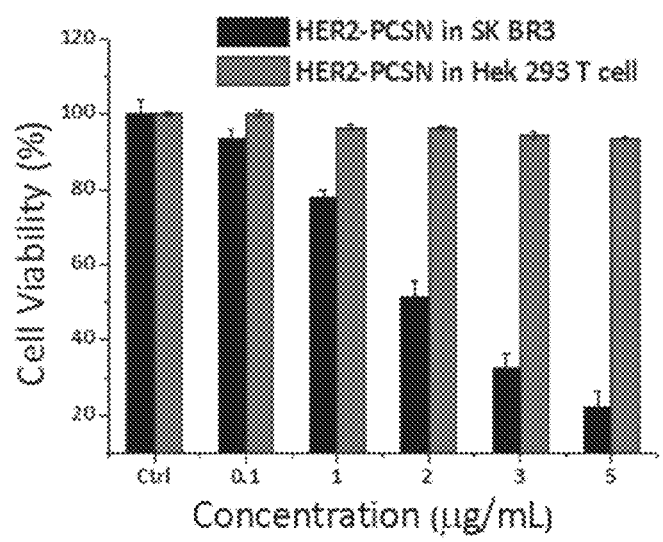

As a result, as shown in FIG. 13, both HER2-PCSNs and EGFR-PCSNs exhibited significant DiI delivery effect and CPT delivery effect on target cancer cells even after stored in vivo environment (FIGS. 13A and 13B), indicating that PCSNs of the present disclosure even in vivo environment may block formation of the protein corona shield surrounded by serum proteins, thereby being used as a drug delivery carrier having in vivo stability and targeting ability. It was also confirmed that CPT-loaded PCSNs may exhibit the specific cell killing effect against SK-BR3 cells which are target cells, and thus it is expected to exhibit a significant anticancer effect when used as a drug delivery carrier (FIG. 13C).

Example 7. Examination of Anticancer Effect of PCSNs In Vivo

In the present disclosure, it was confirmed that PCSNs effectively deliver a drug to target tumor cells in vitro environment to exhibit tumor cell-specific killing effect, and may block formation of a corona shield of serum proteins on the surface to exhibit the stealth effect of avoiding immune responses by macrophages. Accordingly, to examine whether PCSNs of the present disclosure may actually exhibit significant tumor tissue-targeting ability and drug delivery effect in vivo, experiments were performed in vivo environment.

In detail, purchased mice were divided into a total of four groups, each group including 5 mice, and bred in an environment of free access to feed and water. SK-BR3 cells were xenografted to the bred mice to prepare tumor mouse models. Thereafter, saline, DiI-supported MMSNs, PMSNs, and HER2-PCSNs were prepared, and each was intravenously administered to the mouse models which were divided into a total of four groups at a dose of 1 mg/mouse (3 mg/kg, based on DiI). After administering the nanoparticles, while the mice were bred for a total of 24 hr, in-vivo fluorescence imaging was performed to examine distributions of the nanoparticles in the bodies of the mice. In-vivo fluorescence imaging was performed until 28 hr after administration, and then mice were sacrificed to separate hearts, lungs, spleens, livers, kidneys, and tumor tissues, and each organ thus obtained was subjected to ex-vivo fluorescence imaging to examine distributions of DiI in the administered nanoparticles.

Figure 14A:
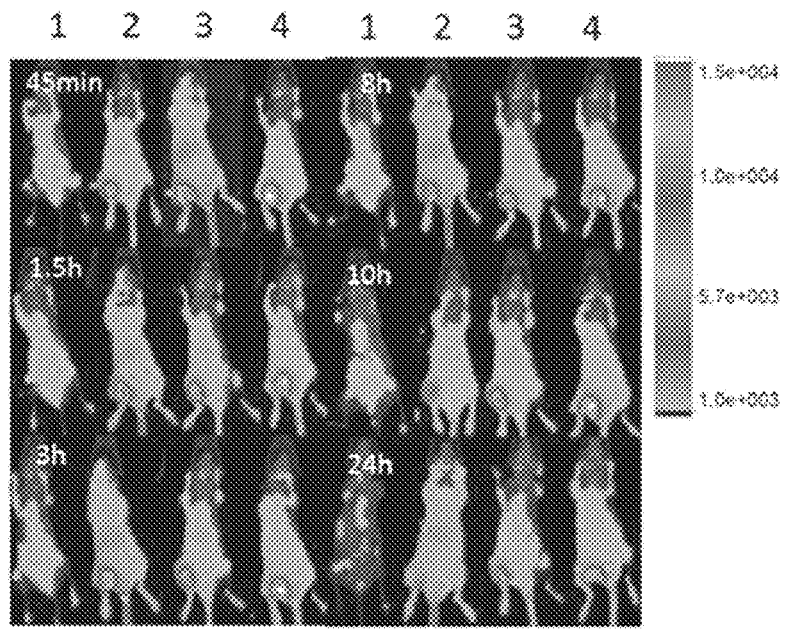
FIGS. 14A and 14B show results of examining fluorescence labels over time, after administering tumor-xenografted mice with CPT-loaded PCSN, PMSN, or HER2-PCSN.
Figure 14B:
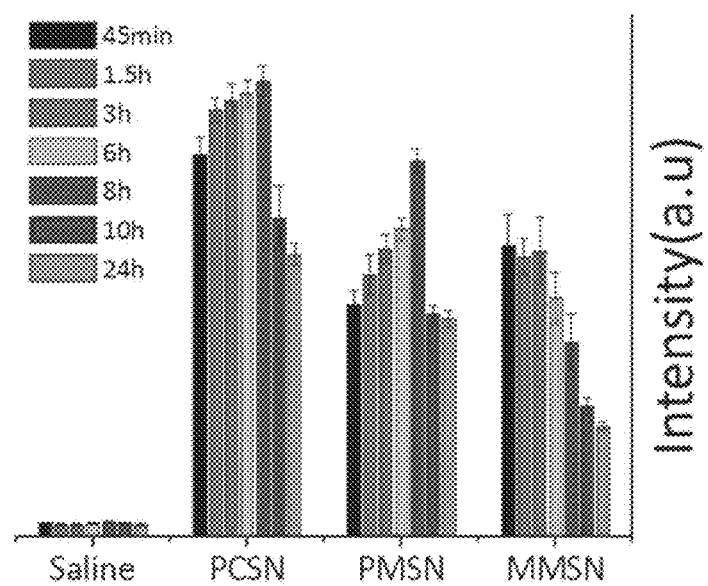

As a result, as shown in FIG. 14, HER2-PCSN-treated group showed a high level of DiI uptake over time, and thus the drug remained in the tumor tissue for 24 hr, whereas PCSN-treated group and PMSN-treated group showed gradual decrease in DiI fluorescence signals which were observed in the early stage of administration, and 24 hr after administration, no fluorescence signals were observed (FIGS. 14A and 14B). These results indicate that when PCSNs are used as a drug delivery carrier, PCSNs exhibit excellent mobility to tumor tissues and persistent residence in the body, as compared with MMSNs and PMSNs commonly used, and therefore, PCSNs are effective as a drug delivery carrier. When DiI fluorescence intensities in tumor tissues were compared between the mouse groups, PCSN-treated group exhibited a significantly high level of DiI fluorescence intensity from the early stage of treatment and also a persistent residence time in the body, as compared with PMSN and MMSN-treated groups (FIG. 14B).

Figure 14C:
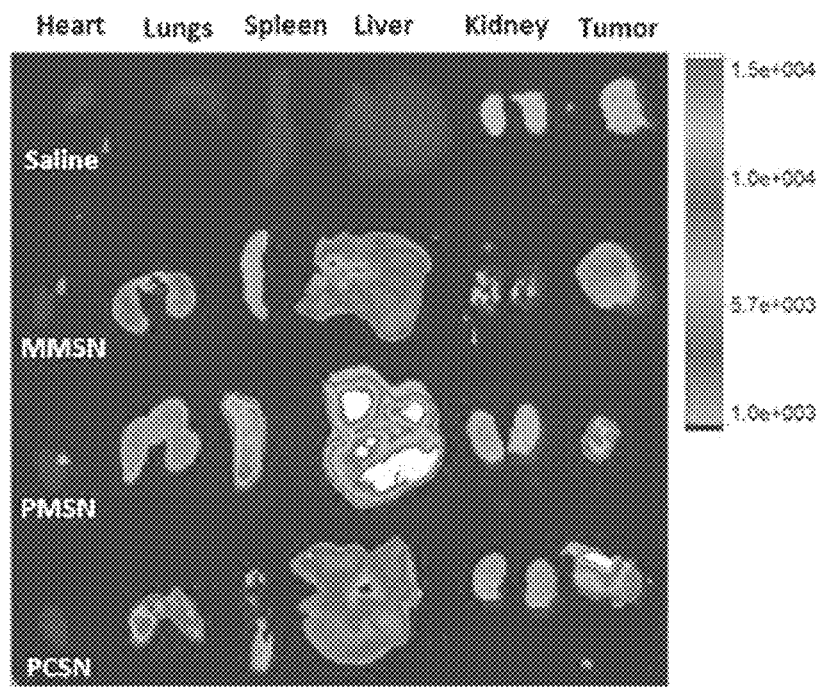
FIGS. 14C and 14D show results of examining fluorescence intensity of tumors of organs which were obtained from mice sacrificed 24 hr after administration.
Figure 14D:
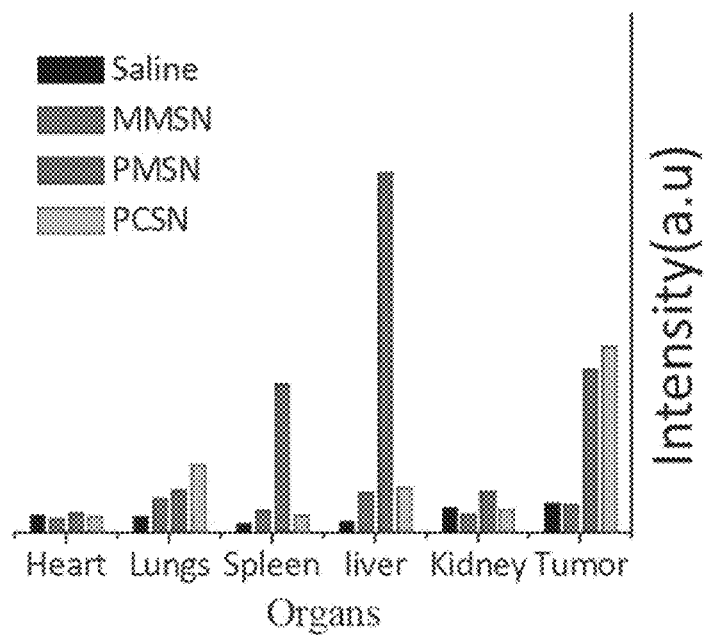

Further, after breeding, the mice were sacrificed and organs were separated, and DiI distributions were examined. DiI fluorescence intensity mostly disappeared in MMSN-treated group 28 hr after administration, and most DiI fluorescence appeared in liver and spleen of PMSN-treated group, indicating that they are discharged by the body's immunity and detoxification (FIGS. 14C and 14D). In contrast, it was confirmed that most DiI dye loaded inside PCSNs remained in the tumor tissue, indicating that PCSNs may safely move to the tumor tissue and may sustain drug release by blocking surrounding of the protein corona shield (FIGS. 14C and 14D).

Figure 15:
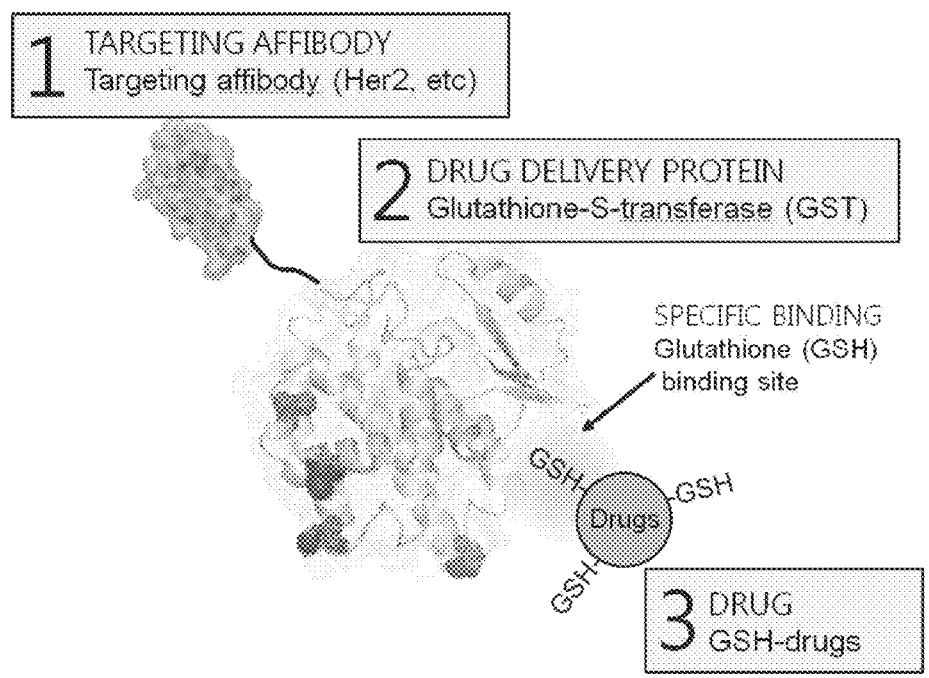
FIG. 15 is an illustration of a structure of a fusion protein according to a specific embodiment and a drug bound thereto.

Example 8. Preparation of Small Molecular Compound Drug Delivery Carrier Using Affibody and GST Fusion Protein In the present embodiment, it was examined whether a drug delivery carrier may be prepared from a small molecular compound, in addition to protein corona shield nanoparticles, by using affibody and GST fusion protein, as shown in FIG. 15.

Figure 16A:
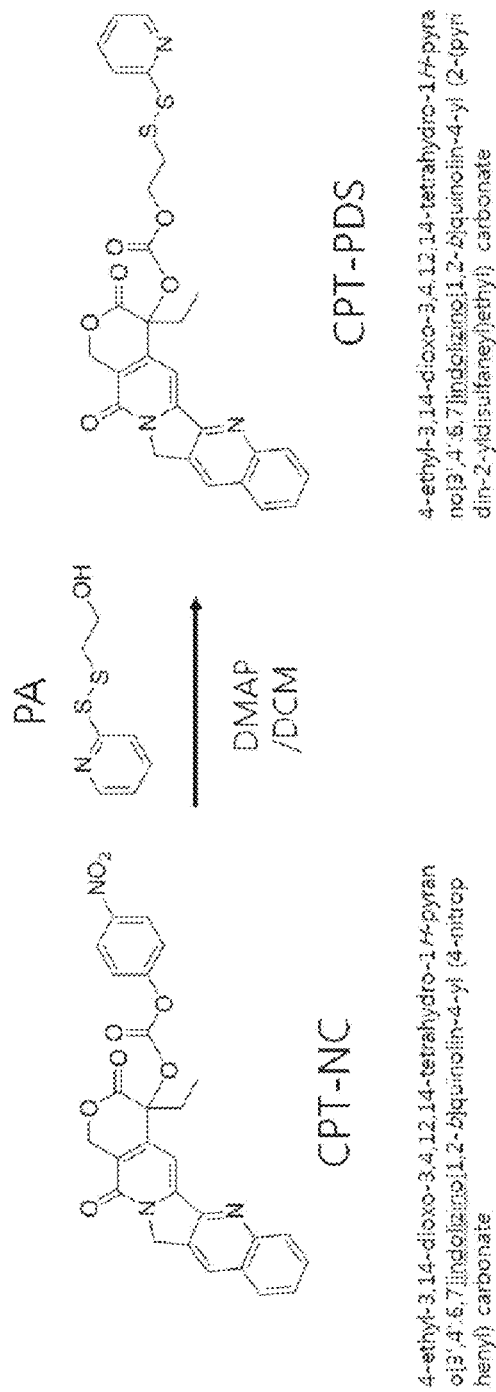
FIG. 16 shows a process of binding camptothecin to the fusion protein according to a specific embodiment (FIG. 16A: a synthesis process of CPT-PDS and FIG. 16B: a synthesis process of GSH-CPT)
Figure 17A:
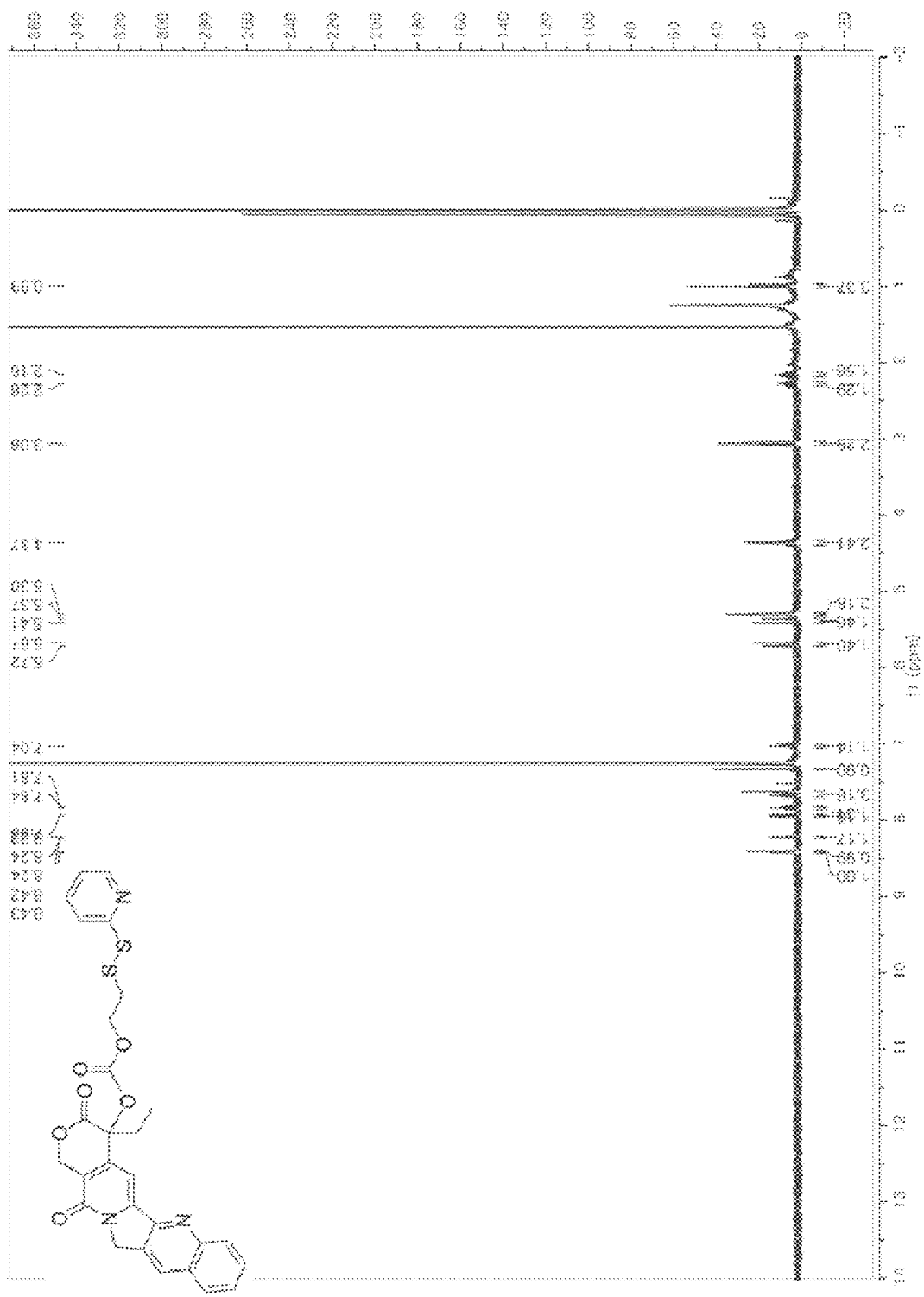
FIG. 17 shows NMR data of CPT-PDS and GSH-CPT (FIG. 17A: NMR data of CPT-PDS and FIG. 17B: NMR data of GSH-CPT)

In detail, as a small molecular compound, camptothecin was used. To conjugate glutathione (GSH) to camptothecin, as shown in FIG. 16A, PA ((2-(pyridin-2-yldisulfaneyl)ethan-1-ol) 52.5 mg, 0.18 mmol) and DMAP (40.6 mg, 0.333 mmol) were mixed with CPT-NC(4-ethyl-3,14-dioxo-3,4,12,14-tetrahydro-1H-pyrano[3',4':6,7]indolizino[1,2-b]quinolin-4-yl(4-nitrophenyl) carbonate) (90 mg, 0.175 mmol) in a dichloromethane (DCM) solution. Then, the mixture was allowed to react at room temperature for 24 hr to prepare CPT-PSD (4-ethyl-3,14-dioxo-3,4,12,14-tetrahydro-1H-pyrano[3',4':6,7]indolizino[1,2-b]quinolin-4-yl (2-(pyridin-2-yldisulfaneyl)ethyl) carbonate). The reacted CPT-PSD mixture was passed through a silica column using a mixed solvent of dichloromethane: ethyl acetate=4:1 to purify CPT-PSD. Mass data thereof are shown in FIG. 17A.

Figure 16B:
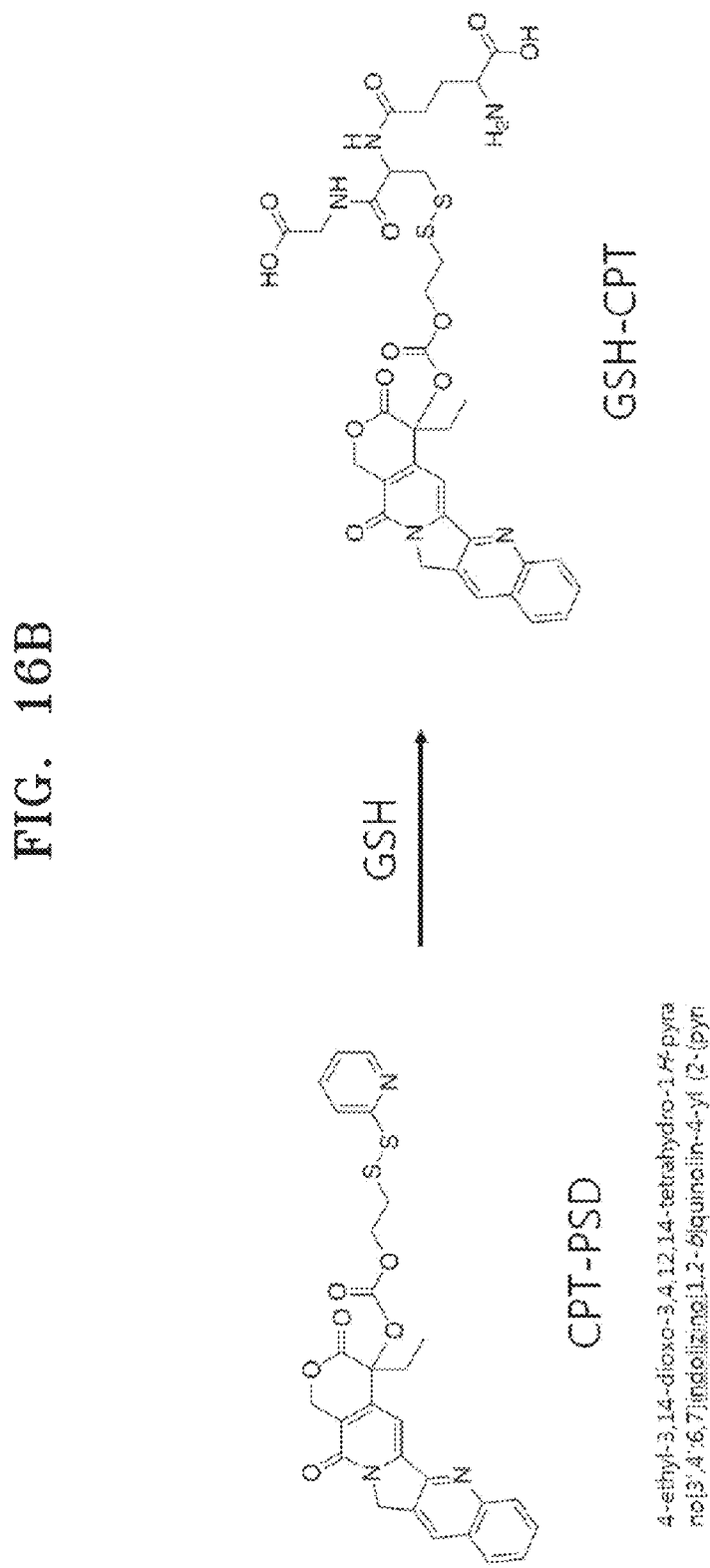
Figure 17B:
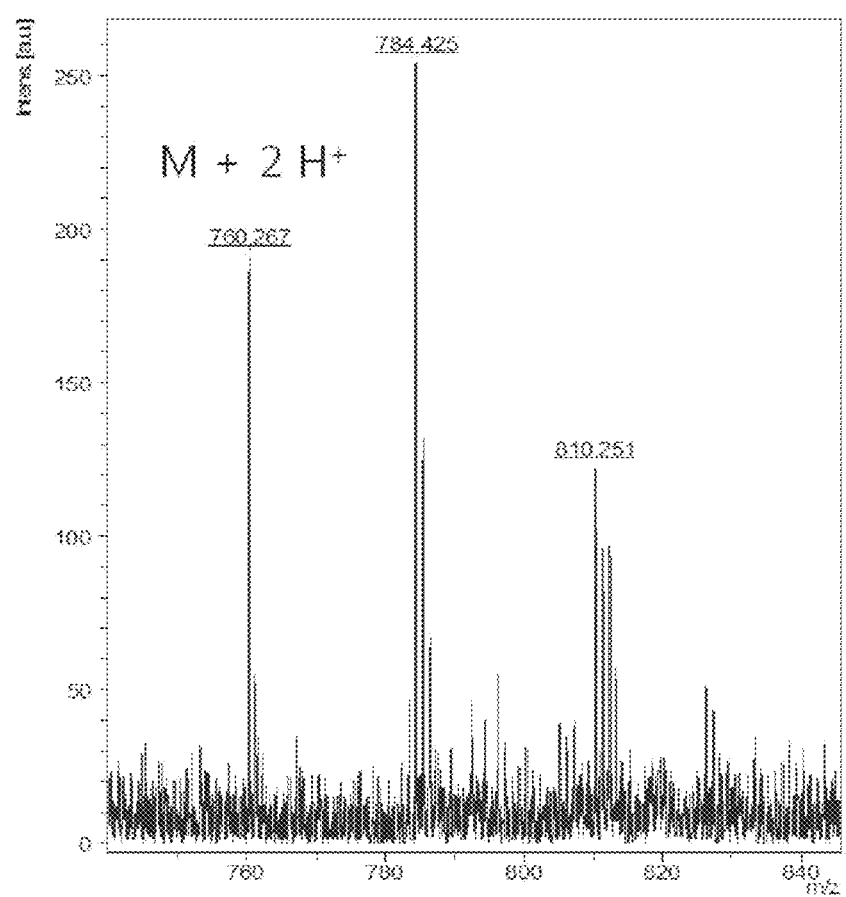

Thereafter, as shown in FIG. 16B, CPT-PDS (10 mg, 0.0178 mmol) and GSH (5.47 mg, 0.0178) were mixed with a PBS solution at pH 7.4 to prepare GSH-conjugated camptothecin by precipitation for 24 hr at room temperature. Mass data thereof are shown in FIG. 17B.

Next, to load the prepared GSH-conjugated camptothecin in GST-HER2 Afb prepared in Example 1, excess GSH-CPT was reacted with GST-HER2 (0.3 mg/ml) at 4° C. for 30 min. Then, excess GSH-CPT was removed by dialysis in PBS (24 hr), and CPT-loaded GST-HER2 Afb was separated.

Example 9. Preparation of Dye Delivery Carrier Using Affibody and GST Fusion Protein In the present embodiment, it was examined whether a drug delivery carrier may be prepared from a dye by using affibody and GST fusion protein.

Figure 18:
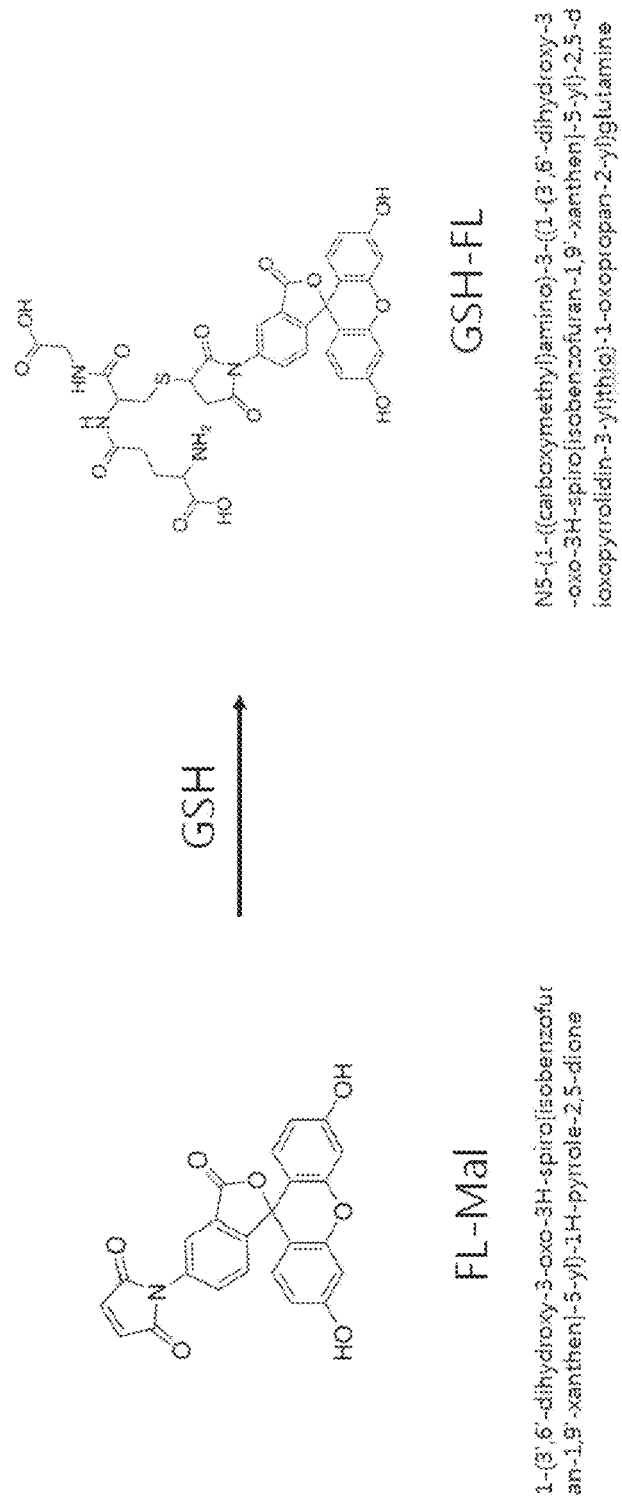
FIG. 18 shows a process of binding a dye to the fusion protein according to a specific embodiment.
Figure 19:
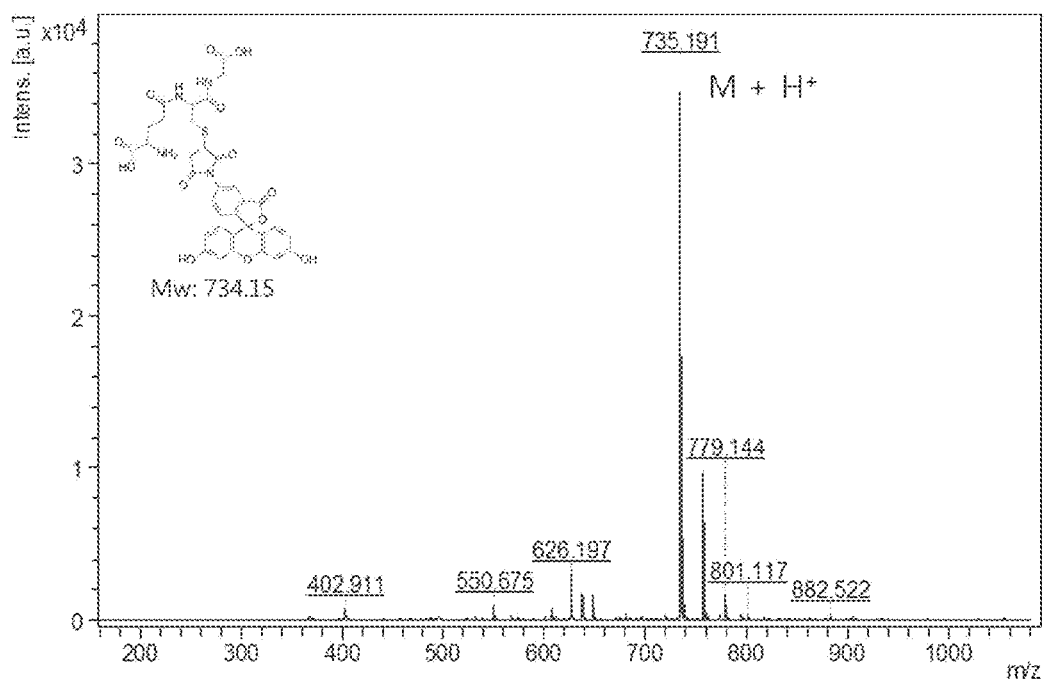
FIG. 19 shows NMR data of GHS-bound dye (GSH-FL).

In detail, as a dye, Fluorescein-Maleimide (FL-Mal) (TCI chemicals) was used. To conjugate GSH to FL-Mal, as shown in FIG. 18A, FL-Mal (1-(4-(3,6-dihydroxy-9H-xanthen-9-yl)phenyl)-1H-pyrrole-2,5-dione) was mixed with GSH (10 mg, 0.0178 mmol) in a PBS solution (5.47 mg, 0.0178), and allowed to react at room temperature for 24 hr, and separated by precipitation to obtain GSH-FL (N5-(1-((carboxymethyl)amino)-3-((1-(4-(3,6-dihydroxy-9H-xanthen-9-yl)phenyl)-2,5-dioxopyrrolidin-3-yl)thio)-1-oxopropan-2-yl)glutamine) (6.18 mg, 46%).

Next, to load the GSH-conjugated FL dye in GST-HER2 Afb prepared in Example 1, excess GSH-FL (1 mg) was reacted with GST-HER2 Afb (0.3 mg/ml) at 4° C. for 30 min. Then, excess FITC-GSH was removed by dialysis in PBS (24 hr), and GSH-FL-loaded GST was separated. Fluorescence emission was measured by irradiation under a UV lamp to confirm loading of GSH-FL in GST.

The invention claimed is:

1. A drug delivery carrier comprising:
   glutathione-S-transferase (GST);
   an affibody, which is a protein having binding affinity for a target cell or a target protein;
   a linker that links the GST with the protein having binding affinity for a target cell or a target protein; and
   a drug bound with the GST via glutathione (GSH).

2. The drug delivery carrier of claim 1, wherein the protein having binding affinity for a target cell or a target protein specifically binds to receptor tyrosine kinases (RTKs).

3. The drug delivery carrier of claim 1, wherein the RTKs are any one selected from the group consisting of epidermal growth factor receptor, insulin receptor, platelet-derived growth factor receptor, vascular endothelial growth factor receptor, fibroblast growth factor receptor, cholecystokinin (CCK) receptor, neurotrophic factor (NGF) receptor, hepatocyte growth factor (HGF) receptor, ephrin (Eph) receptor, angiopoietin receptor, and related to receptor tyrosine kinase (RYK) receptor.

4. The drug delivery carrier of claim 1, wherein the drug is a nanoparticle capable of loading a drug.

5. The drug delivery carrier of claim 4, wherein the nanoparticle is any one selected from the group consisting of a mesoporous silica nanoparticle (MSN), a gold nanoparticle, a magnetic nanoparticle, a nucleic acid-metal organic framework nanoparticle, and a polymer nanoparticle.

6. The drug delivery carrier of claim 5, wherein the GSH is bound onto the surface of the nanoparticle.

7. The drug delivery carrier of claim 1, wherein the drug is an anticancer agent.

8. A pharmaceutical composition for preventing or treating cancer, the pharmaceutical composition comprising:
   glutathione-S-transferase (GST);
   an affibody, which is a protein having binding affinity for a target cell or a target protein;
   a linker that links the GST with the protein having binding affinity for a target cell or a target protein; and
   an anticancer agent bound with the GST via glutathione (GSH).

9. The pharmaceutical composition for preventing or treating cancer of claim 8, wherein the protein having binding affinity for a target cell or a target protein specifically binds to an epidermal growth factor receptor, an insulin receptor, a platelet-derived growth factor receptor, a vascular endothelial growth factor receptor, or an angiopoietin receptor.

10. The pharmaceutical composition for preventing or treating cancer of claim 8, wherein the anticancer agent is an anticancer agent-loaded nanoparticle.

11. A method of delivering a drug to an individual, the method comprising administering a composition comprising glutathione-S-transferase (GST); an affibody, which is a protein having binding affinity for a target cell; a linker that links the GST with the protein having binding affinity for a target cell; and a drug bound with the GST via glutathione (GSH) to an individual in need thereof.

12. A method of preventing or treating cancer, the method comprising administering a composition comprising glutathione-S-transferase (GST); an affibody, which is a protein having binding affinity for a target cell; a linker that links the GST with the protein having binding affinity for a target cell; and an anticancer agent bound with the GST via glutathione (GSH) to an individual in need thereof.

* * * * *

SEQUENCE LISTING

<160> NUMBER OF SEQ ID NOS: 12

<210> SEQ ID NO 1
<211> LENGTH: 25
<212> TYPE: PRT
<213> ORGANISM: Artificial Sequence
<220> FEATURE:
<223> OTHER INFORMATION: Linker domain

<400> SEQUENCE: 1

Gly Gly Gly Leu Val Pro Arg Gly Ser Gly Gly Gly Cys Gly Gly Gly
1               5                   10                  15

Gly Thr Gly Gly Gly Ser Gly Gly Gly
            20                  25

```
<210> SEQ ID NO 2
<211> LENGTH: 5
<212> TYPE: PRT
<213> ORGANISM: Artificial Sequence
<220> FEATURE:
<223> OTHER INFORMATION: Linker 1

<400> SEQUENCE: 2

Gly Gly Gly Gly Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Linker 2

<400> SEQUENCE: 3

Ser Gly Gly Gly Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Linker 3

<400> SEQUENCE: 4

Ser Arg Ser Ser Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Linker 4

<400> SEQUENCE: 5

Ser Gly Ser Ser Cys
1               5

<210> SEQ ID NO 6
<211> LENGTH: 12
<212> TYPE: PRT
<213> ORGANISM: Artificial Sequence
<220> FEATURE:
<223> OTHER INFORMATION: Linker 5

<400> SEQUENCE: 6

Gly Lys Ser Ser Gly Ser Gly Ser Glu Ser Lys Ser
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Linker 6

<400> SEQUENCE: 7

Arg Pro Pro Pro Pro Cys
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Linker 7

<400> SEQUENCE: 8

Ser Ser Pro Pro Pro Pro Cys
1               5

<210> SEQ ID NO 9
<211> LENGTH: 14
<212> TYPE: PRT
<213> ORGANISM: Artificial Sequence
<220> FEATURE:
<223> OTHER INFORMATION: Linker 8

<400> SEQUENCE: 9

Gly Ser Thr Ser Gly Ser Gly Lys Ser Ser Glu Gly Lys Gly
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Linker 9

<400> SEQUENCE: 10

Gly Ser Thr Ser Gly Ser Gly Lys Ser Ser Glu Gly Ser Gly Ser Thr
1               5                   10                  15

Lys Gly

<210> SEQ ID NO 11
<211> LENGTH: 18
<212> TYPE: PRT
<213> ORGANISM: Artificial Sequence
<220> FEATURE:
<223> OTHER INFORMATION: Linker 10

<400> SEQUENCE: 11

Gly Ser Thr Ser Gly Ser Gly Lys Pro Gly Ser Gly Glu Gly Ser Thr
1               5                   10                  15

Lys Gly

<210> SEQ ID NO 12
<211> LENGTH: 14
<212> TYPE: PRT
<213> ORGANISM: Artificial Sequence
<220> FEATURE:
<223> OTHER INFORMATION: Linker 11

<400> SEQUENCE: 12

Glu Gly Lys Ser Ser Gly Ser Gly Ser Glu Ser Lys Glu Phe
1               5                   10
```